(12) United States Patent
Ilkow et al.

(10) Patent No.: US 10,604,741 B2
(45) Date of Patent: Mar. 31, 2020

(54) COMPOSITIONS AND METHODS FOR ENHANCING VIRUS REPLICATION

(71) Applicant: TURNSTONE LIMITED PARTNERSHIP, Toronto (CA)

(72) Inventors: Carolina Solange Ilkow, Ottawa (CA); Fabrice Le Boeuf, Gatineau (CA); John Cameron Bell, Ottawa (CA); Jean-Simon Diallo, Ottawa (CA); Rozanne Arulanandam, Orleans (CA)

(73) Assignee: TURNSTONE LIMITED PARTNERSHIP, Toronto (CA)

( * ) Notice: Subject to any disclaimer, the term of this patent is extended or adjusted under 35 U.S.C. 154(b) by 0 days.

(21) Appl. No.: 15/919,554

(22) Filed: Mar. 13, 2018

(65) Prior Publication Data

US 2018/0237753 A1    Aug. 23, 2018

Related U.S. Application Data

(63) Continuation of application No. 14/898,083, filed as application No. PCT/CA2014/050564 on Jun. 16, 2014, now Pat. No. 10,066,214.

(60) Provisional application No. 61/835,446, filed on Jun. 14, 2013.

(51) Int. Cl.

| | |
|---|---|
| *A01N 63/00* | (2020.01) |
| *A61K 35/76* | (2015.01) |
| *A61K 35/766* | (2015.01) |
| *A61K 35/768* | (2015.01) |
| *A61K 38/17* | (2006.01) |
| *C12N 7/00* | (2006.01) |
| *C07K 14/50* | (2006.01) |
| *A61K 38/18* | (2006.01) |

(52) U.S. Cl.
CPC ............... *C12N 7/00* (2013.01); *A61K 35/76* (2013.01); *A61K 35/766* (2013.01); *A61K 35/768* (2013.01); *A61K 38/1793* (2013.01); *A61K 38/1825* (2013.01); *C07K 14/50* (2013.01); *C07K 2319/02* (2013.01); *C12N 2710/16651* (2013.01); *C12N 2710/24151* (2013.01); *C12N 2720/12051* (2013.01); *C12N 2760/16151* (2013.01); *C12N 2760/16152* (2013.01); *C12N 2760/18451* (2013.01); *C12N 2760/18452* (2013.01); *C12N 2760/20232* (2013.01); *C12N 2760/20251* (2013.01); *Y02A 50/385* (2018.01); *Y02A 50/393* (2018.01); *Y02A 50/465* (2018.01)

(58) Field of Classification Search
CPC ............ A61K 2300/00; A61K 38/1793; A61K 38/1825; A61K 35/76; A61K 35/766
See application file for complete search history.

(56) References Cited

U.S. PATENT DOCUMENTS

| | | |
|---|---|---|
| 6,685,934 B1 | 2/2004 | Mallet et al. |
| 2016/0130563 A1 | 5/2016 | Ilkow et al. |

FOREIGN PATENT DOCUMENTS

| | | | |
|---|---|---|---|
| EP | 2064229 B1 | | 8/2015 |
| WO | 0119380 A2 | | 3/2001 |
| WO | 2004085658 A1 | | 10/2004 |
| WO | 2009016433 A2 | | 2/2009 |
| WO | WO2011070440 | * | 11/2010 |
| WO | 2011003191 A1 | | 1/2011 |
| WO | 2011070440 A2 | | 6/2011 |

OTHER PUBLICATIONS

European Patent Application No. 14811047.1, Office Action dated Mar. 23, 2018.
U.S. Appl. No. 14/898,083, Notice of Allowance dated May 31, 2018.
Bozoky et al., "Novel Signatures of Cancer-Associated Fibroblasts," International Journal of Cancer, Jul. 2013, vol. 133 (2), pp. 1-8.
Breitbach et al., "Oncolytic Vaccinia Virus Disrupts Tumor-Associated Vasculature in Humans," Cancer Research, Feb. 2013, vol. 73 (4), pp. 1265-1275.
Brun et al., "Identification of Genetically Modified Maraba Virus as an Oncolytic Rhabdovirus," Molecular Therapy, Aug. 2010, vol. 18 (8), pp. 1440-1449.
Chlebova et al., "High Molecular Weight FGF2: the Biology of a Nuclear Growth Factor," Cellular and Molecular Life Sciences, Jan. 2009, vol. 66 (2), pp. 225-235.
Cirri et al., "Cancer Associated Fibroblasts: the Dark Side of the Coin," American Journal of Cancer Research, Apr. 2011, vol. 1 (4), pp. 482-497.
Colamonici et al., "Vaccinia Virus B18R Gene Encodes a Type I Interferon-binding Protein That Blocks Interferon Alpha Transmembrane Signaling," The Journal of Biological Chemistry, Jul. 1995, vol. 270 (27), pp. 15974-15978.
Critchley-Thorne et al., "Impaired Interferon Signaling is a Common Immune Defect in Human Cancer," Proceedings of the National Academy of Sciences, Jun. 2009, vol. 106 (22), pp. 9010-9015.

(Continued)

*Primary Examiner* — Barry A Chestnut
(74) *Attorney, Agent, or Firm* — Borden Ladner Gervais LLP; David Nauman

(57) ABSTRACT

Described herein is a method of enhancing virus replication in permissive cells that express a receptor to FGF2 protein. The method includes administering FGF2 protein or a functional variant thereof and the virus to the permissive cells. An oncolytic virus having a genome that includes an open reading frame that encodes FGF2 protein or a functional variant thereof is also described.

14 Claims, 14 Drawing Sheets

Specification includes a Sequence Listing.

(56) References Cited

OTHER PUBLICATIONS

Diallo et al., "Ex Vivo Infection of Live Tissue with Oncolytic Viruses," The Journal of Visualized Experiments, Jun. 2011, (52), e2854, doi:10.3791/2854.
European Patent Application No. 14811047.1, Extended European Search Report, dated Nov. 8, 2016.
Fu et al., "Incorporation of the B18R Gene of Vaccinia Virus Into an Oncolytic Herpes Simplex Virus Improves Antitumor Activity," Molecular Therapy, Oct. 2012, vol. 20 (10), pp. 1871-1881.
Goldufsky et al., "Oncolytic Virus Therapy for Cancer," Oncolytic Virotherapy, Sep. 2013, vol. 2, pp. 31-46.
International Patent Application No. PCT/CA2014/050564, International Preliminary Report on Patentability dated Dec. 15, 2015.
International Patent Application No. PCT/CA2014/050564, International Search Report and Written Opinion dated Aug. 28, 2014.
Jenks et al., "Safety Studies on Intrahepatic or Intratumoral Injection of Oncolytic Vesicular Stomatitis Virus Expressing Interferon-Beta in Rodents and Nonhuman Primates," Human Gene Therapy, Apr. 2010, vol. 21 (4), pp. 451-462.
Kalluri et al., "Fibroblasts in Cancer," Nature, May 2006, vol. 6 (5), pp. 392-401.
Kim et al., "Application of FGF-2 to Modulate Herpetic Stromal Keratitis," Current Eye Research, Dec. 2006, vol. 31 (12), pp. 1021-1028.
Levy et al., "The Virus Battles: IFN Induction of the Antiviral State and Mechanisms of Viral Evasion," Cytokine and Growth Factor Reviews, Jun. 2001, vol. 12 (2-3), pp. 143-156.
Rogelj et al., "Basic Fibroblast Growth Factor Fused to a Signal Peptide Transforms Cells," Nature, Jan. 1988, vol. 331 (6152), pp. 173-175.
Seet et al., "Viral Chemokine-Binding Proteins," Journal of Leukocyte Biology, Jul. 2002, vol. 72 (1), pp. 24-34.
Strutz et al., "Renal Fibroblasts and Myofibroblasts in Chronic Kidney Disease," Journal of the American Society of Nephrology, Nov. 2006, vol. 17 (11), pp. 2992-2998.
Togo et al., "Carcinoma-Associated Fibroblasts are a Promising Therapeutic Target," Cancers, Jan. 2013, vol. 5 (1), pp. 149-169.
U.S. Appl. No. 14/898,083, Non-Final Office Action dated Aug. 9, 2017.
U.S. Appl. No. 14/898,083, Restriction Requirement dated Jan. 20, 2017.
Zaidi et al., "The Two Faces of Inerferon-y in Cancer," Clinical Cancer Research, Oct. 2011, vol. 17 (19), pp. 6118-6124.

\* cited by examiner

COMPOSITIONS AND METHODS FOR ENHANCING VIRUS REPLICATION

CROSS REFERENCE TO RELATED APPLICATIONS

This application is a continuation of U.S. patent application Ser. No. 14/898,083 filed Dec. 11, 2015, which is a national phase entry of PCT/CA2014/050564 filed on Jun. 16, 2014, which claims the benefit of priority of U.S. Provisional Patent Application No. 61/835,446 filed Jun. 14, 2013, which is hereby incorporated by reference.

INCORPORATION OF SEQUENCE LISTING

This application includes a computer readable form of the Sequence Listing "PAT_7522AW-2_seqlisting.txt", created on Mar. 9, 2018 and containing 35 kilobytes in size, is herein incorporated by reference.

FIELD

The present disclosure relates to compositions, methods and uses that enhance and/or accelerate viral growth, spread or cytotoxicity.

BACKGROUND

The following discussion is not an admission that anything discussed below is citable as prior art or common general knowledge.

Viral vaccines have been used to protect against diseases and improve human and animal health. Viral vaccines are already used, or are being developed, to treat infectious diseases such as: *influenza*, West Nile disease, dengue fever, HIV, rabies, *influenza, hepatitis A*, and poliovirus.

Viral vaccines may use live and attenuated viruses, or killed viruses produced by inactivating viruses after growth in cell culture. Live, attenuated viral vaccines may take advantage of weakened or attenuated strains of the virus in order to induce an immune response in the immunized animal or human. Killed virus vaccines may induce immune responses due to the presence of high concentrations of antigen present. On upon subsequent exposure to a pathogenic strain of the virus, the immunized individual is protected from disease.

Oncolytic viruses (OV) are being developed as replicating therapeutics selected or designed to preferentially grow in and kill cancer cells. Due to the self-replicating nature of OVs, the principle challenge in OV therapy is not initial saturation of all the tumors but rather efficient spreading within tumor cells upon infection of a reasonable amount of cancerous tissue. OVs may be genetically modified or selected for attenuated growth. OVs may take advantage of cellular pathways that are aberrantly regulated in cancer cells. While this limits the spread of OVs in normal host tissues, it can also blunt their natural ability to rapidly spread within and between tumors.

Examples of viruses which have been used for viral vaccines, oncolytic viruses, or both, include: influenza virus, adenovirus, vaccinia virus, dengue virus, herpes simplex virus, poliovirus, reovirus, senecavirus, rhabdoviruses, Newcastle Disease virus, moribilivirus (Measles virus) and Modified vaccinia Ankara.

It is desirable to be able to enhance virus growth ex vivo, for example when producing viruses for viral vaccines, gene therapy or as therapeutic agents such as oncolytic viruses. It is also desirable to be able to enhance virus growth in vivo, for example to enhance spreading of oncolytic viruses within tumor cells upon infection of a reasonable amount of cancerous tissue. Such enhanced growth of oncolytic virus would result in greater cytotoxicity to the cancer.

There is a need in the art to identify compounds, methods and uses that enhance virus growth, spread or cytotoxicity.

SUMMARY

The following discussion is intended to introduce the reader to the detailed description to follow, and not to limit or define any claimed invention.

In a first aspect, the present disclosure provides a method of enhancing virus replication in permissive cells that express a receptor to FGF2 protein. The method includes administering FGF2 protein or a functional variant thereof and the virus to the permissive cells.

The FGF2 protein or functional variant thereof may further include an amino acid sequence of an immunoglobulin signal peptide. The amino acid sequence of the immunoglobulin signal peptide may include the sequence of SEQ ID NO: 1.

The FGF2 protein may include an amino acid sequence selected from SEQ ID NOs: 2-13. The functional variant of the FGF2 protein may include an amino acid sequence that is at least 90% identical, such as at least 95%, 98% or 99% identical, to any one of the sequences of SEQ ID NO: 2-12.

Enhancing virus replication may include: (a) producing a greater number of virus particles using the permissive cells in a given time, (b) increasing the rate of production of virus particles using the permissive cells at a given time, (c) reducing the multiplicity of infection (MOI) needed to produce the same number of virus particles, (d) reducing the MOI needed to produce virus particles at the same rate, or (e) any combination thereof, when compared to identical growth conditions without the FGF2 protein or functional variant thereof being administered to the permissive cells.

The permissive cells that express a receptor to FGF2 protein may be cancer cells, such as adenocarcinoma cells, pancreatic carcinoma cells, ovarian carcinoma cells, renal carcinoma cells, or colon carcinoma cells. The permissive cells that express a receptor to FGF2 protein may be activated fibroblast cells, such as activated human fetal fibroblast cells or cancer-associated fibroblast cells. The activated human fetal fibroblast cells may be WI38 cells or MRC5 cells.

The virus may be a rhabdovirus, a *vaccinia virus, herpes simplex virus*-1, reovirus, *measles virus*, Modified *Vaccinia Ankara* virus, NewCastle Disease virus, *influenza virus, West Nile virus, dengue virus*, HIV, rabies virus, *hepatitis virus*, or poliovirus. The rhabdovirus may be vesicular stomatitis virus, VSVΔ51, VSV IFN-β, *maraba virus*, or MG1 virus.

The permissive cells may be cultured cells and administering the FGF2 protein or functional variant thereof to the permissive cells may include adding to the permissive cell culture a composition comprising the FGF2 or functional variant thereof and a carrier or diluent. The FGF2 protein or functional variant thereof may be administered to the permissive cells in a final concentration that is greater than or equal to 1 ng/mL, for example the final concentration may be between 5 ng/mL and 100 ng/mL.

The FGF2 protein or functional variant thereof may be administered to the permissive cells before, or at the same time that, the virus is administered to the permissive cell. The FGF2 protein or functional variant thereof may be administered to the permissive cells after the virus is administered to the permissive cell.

The permissive cells may be cultured cells and administering the FGF2 protein to the permissive cells may include adding to the permissive cell culture an oncolytic virus having a genome comprising an open reading frame that encodes the FGF2 protein or functional variant thereof. The oncolytic virus may be administered at an MOI greater than 0.001, such as an MOI between about 0.01 and about 0.1.

The permissive cells may be cancer cells in an animal and administering the FGF2 protein or functional variant thereof and the virus to the cancer cells may include administering an oncolytic virus having a genome comprising an open reading frame that encodes the FGF2 protein or functional variant thereof. The oncolytic virus may be administered at a quantity greater than 1e5 pfu/animal. When the animal is a human being, the oncolytic virus may be administered at a quantity between about 1e7 pfu and about 1e13 pfu/human.

The method may also further include administering to the permissive cells a Type 1 interferon scavenger, such as a B18R protein. The B18R protein may include an amino acid sequence according to SEQ ID NO: 15, 16 or 17.

In another aspect, there is provided an isolated oncolytic virus particle having a genome comprising an open reading frame that encodes FGF2 protein or a functional variant thereof. The FGF2 protein or functional variant thereof may further include an amino acid sequence of an immunoglobulin signal peptide. The amino acid sequence of the immunoglobulin signal peptide may include the sequence of SEQ ID NO: 1.

The FGF2 protein may include an amino acid sequence selected from SEQ ID NOs: 2-13. The functional variant of FGF2 protein may include an amino acid sequence that is at least 90% identical, such as at least 95%, 98% or at least 99% identical, to any one of the sequences of SEQ ID NO: 2-12.

The genome may further include an open reading frame that encodes a Type 1 interferon scavenger, such as a B18R protein. The B18R protein may include an amino acid sequence according to SEQ ID NO: 15, 16 or 17.

The oncolytic virus may be a rhabdovirus, a *vaccinia virus*, or a *herpes simplex virus*-1. The rhabdovirus may be vesicular stomatitis virus, VSVΔ51, VSV IFN-β, *maraba virus*, or MG1 virus.

In another aspect, there is provided a use of FGF2 protein, or a functional variant thereof, for enhancing virus replication in permissive cells that express a receptor to FGF2 protein.

The FGF2 protein or functional variant thereof may further include an amino acid sequence of an immunoglobulin signal peptide. The amino acid sequence of the immunoglobulin signal peptide may include the sequence of SEQ ID NO: 1.

The FGF2 protein may include an amino acid sequence selected from SEQ ID NOs: 2-13. The functional variant of FGF2 protein may include an amino acid sequence that is at least 90% identical, such as at least 95%, 98% or at least 99% identical, to any one of the sequences of SEQ ID NO: 2-12.

Enhancing virus replication may include: (a) producing a greater number of virus particles using the permissive cells in a given time, (b) increasing the rate of production of virus particles using the permissive cells at a given time, (c) reducing the multiplicity of infection (MOI) needed to produce the same number of virus particles, (d) reducing the MOI needed to produce virus particles at the same rate, or (e) any combination thereof, when compared to identical growth conditions without the FGF2 protein or functional variant thereof being administered to the permissive cells.

The permissive cells that express a receptor to FGF2 protein may be cancer cells, such as adenocarcinoma cells, pancreatic carcinoma cells, ovarian carcinoma cells, renal carcinoma cells, or colon carcinoma cells.

The permissive cells that express a receptor to FGF2 protein may be activated fibroblast cells. The activated fibroblast cells may be activated human fetal fibroblast cells or cancer-associated fibroblast cells. The activated human fetal fibroblast cells may be WI38 cells or MRC5 cells.

The virus may be a rhabdovirus, a *vaccinia virus, herpes simplex virus*-1, reovirus, *measles virus*, Modified Vaccinia Ankara virus, Newcastle Disease virus, *influenza virus, West Nile virus, dengue virus*, HIV, rabies virus, *hepatitis virus*, or poliovirus. The rhabdovirus may be vesicular stomatitis virus, VSVΔ51, VSV IFN-β, *maraba virus*, or MG1 virus.

The permissive cells may be cultured cells. The FGF2 protein or functional variant thereof may be formulated for administration to the permissive cells in a final concentration that is greater than or equal to 1 ng/mL, such as a final concentration between 5 ng/mL and 100 ng/mL.

The FGF2 protein or functional variant thereof may be formulated for administration to the permissive cells before, or at the same time that, the virus is administered to the permissive cell.

The FGF2 protein or functional variant thereof may be formulated for administration to the permissive cells after the virus is administered to the permissive cell.

The permissive cells may be cultured cells and the FGF2 protein may be formulated for administration to the permissive cells using an oncolytic virus having a genome comprising an open reading frame that encodes the FGF2 protein or functional variant thereof. The oncolytic virus may be formulated for administration at an MOI greater than 0.001, such as at an MOI between about 0.01 and about 0.1.

The permissive cells may be cancer cells in an animal and the FGF2 protein or functional variant thereof may be formulated for administration to the cancer cells using an oncolytic virus having a genome comprising an open reading frame that encodes the FGF2 protein or functional variant thereof. The oncolytic virus may be formulated for administration in a quantity greater than 1e5 pfu/animal. When the animal is a human being, the oncolytic virus may be formulated for administration in at a quantity between about 1e7 pfu and about 1e13 pfu/human.

The FGF2 protein may be formulated for administration in combination with a Type 1 interferon scavenger, such as a B18R protein. The B18R protein may include an amino acid sequence according to SEQ ID NO: 15, 16 or 17.

Other aspects and features of the present disclosure will become apparent to those ordinarily skilled in the art upon review of the following description of specific examples in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
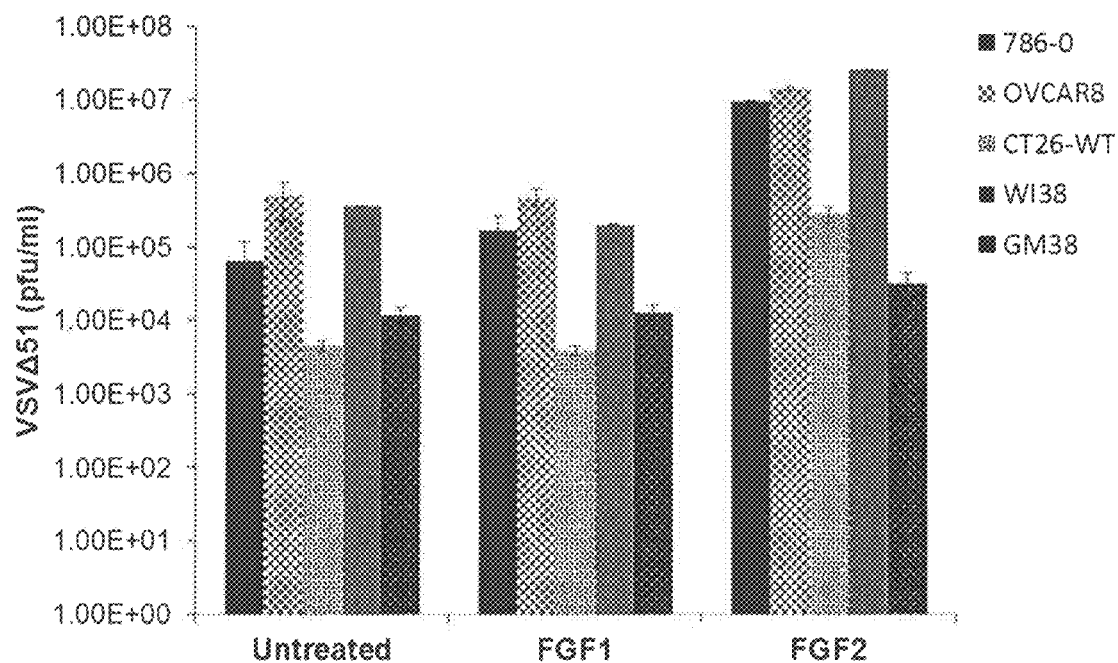
FIG. 1 is a graph illustrating VSVΔ51 replication in different cell lines that were untreated, or administered with FGF1 or FGF2.

Generally, the present disclosure provides a method of enhancing virus replication in permissive cells that express a receptor to fibroblast growth factor 2 (FGF2) protein. The permissive cell may express FGF Receptor 1, FGF Receptor 3, or both. The method includes administering FGF2 protein, or a functional variant thereof, and a viable virus to the permissive cells.

The present disclosure also provides: the use of FGF2 protein, or a functional variant thereof, for enhancing virus production in the permissive cells that express a receptor to FGF2 protein; as well as FGF2 protein, or a functional variant thereof, for enhancing virus replication in the permissive cells that express a receptor to FGF2 protein. Both general and specific examples of the methods discussed herein would be understood to equally apply to: the use of the FGF2 protein or functional variant thereof for enhancing the virus replication in the permissive cells that express a receptor to FGF2 protein; as well as to the FGF2 protein or functional variant thereof for enhancing the virus replication in the permissive cells that express a receptor to FGF2 protein.

FGF2 protein is also known as "basic fibroblast growth factor", "bFGF", and "FGF-β". The FGF2 protein, or the functional variant thereof, may be modified to additionally include an amino acid sequence of an immunoglobulin signal peptide (IgSP). The IgSP may be at the N-terminal end of the FGF2-protein, or functional variant thereof. Adding the IgSP sequence may enhance secretion of the FGF2 protein or functional variant, as described in S. Rogelj, R. A. Weinberg, P. Fanning and M. Klagsbrun: Basic Fibroblast Growth Factor (bFGF) Fused to a Signal Peptide Transforms Cells. Nature, 331(6152): 173-175 (1988).

The amino acid sequence of IgSP may be: MKCSWVIF-FLMAVVTGVNS (SEQ ID NO: 1).

Specific examples of FGF2 protein include proteins having the following amino acid sequences:

```
                                            (SEQ ID NO: 2)
---MAAGSIT TLPALPEDGG SG-AFPPGHF KDPKRLYCKN

GGFFLRIHPD GRVDGVREKS DPHIKLQLQA EERGVVSIKG

VCANRYLAMK EDGRLLASKC VTDECFFFER LESNNYNTYR

SRKYTSWYVA LKRTGQYKLG SKTGPGQKAI LFLPMSAKS (SEQ ID NO: 3)
---MAASGIT SLPALPEDGG --AAFPPGHF KDPKRLYCKN

GGFFLRIHPD GRVDGVREKS DPHVKLQLQA EERGVVSIKG

VCANRYLAMK EDGRLLASKC VTEECFFFERLESNNYNTYRS

RKYSSWYVALKRTGQYKLGSKTGPGQKAI LFLPMSAKS (SEQ ID NO: 4)
MAAGAAGSIT TLPALPDDGG GG-AFPPGHF KDPKRLYCKN

GGFFLRINPD GRVDGVREKS DPHIKLQLQA EERGVVSIKG

VSANRFLAMK EDGRLLALKC ATEECFFFER LESNNYNTYR

SRKYSDWYVA LKRTGQYKPG PKTGPGQKAI LFLPMSAKS (SEQ ID NO: 5)
---MAAGSIT TLPALSGDGG GGGAFPPGHF KDPKRLYCKN

GGFFLRIHPD GRVDGIREKS DPNIKLQLQA EERGVVSIKG

VCANRYLAMK EDGRLLALKY VTEECFFFER LESNNYNTYR

SRKYSNWYVA LKRTGQYKLG SKTGPGQKAI LFLPMSAKS (SEQ ID NO: 6)
---MAAGSIT TLPALPEDGG SS-AFPPGHF KDPKRLYCKN

GGFFLRIHPD GRVDGVREKS DPHIKLQLQA EERGVVSIKG

VCANRYLAMK EDGRLLASKC VTDECFFFER LESNNYNTYR

SRKYSSWYVA LKRTGQYKLG PKTGPGQKAI LFLPMSAKS (SEQ ID NO: 7)
---MAAGSIT TLPSLPEDGG SG-AFPPGHF KDPKRLYCKN

GGFFLRIHPD GRVDGVREKS DPHIKLQLQA EERGVVSIKG
```

```
VCANRYLAMK EDGRLLASKC VTDECFFFER LESNNYNTYR

SRKYSSWYVA LKRTGQYKLG PKTGPGQKAI LFLPMSAKS (SEQ ID NO: 8)
---MAAGSIT SLPALPEDGG -G-AFPPGHF KDPKRLYCKN

GGFFLRIHPD GRVDGVREKS DPHVKLQLQA EERGVVSIKG

VCANRYLAMK EDGRLLASKC VTEECFFFER LESNNYNTYR

SRKYSSWYVA LKRTGQYKLG SKTGPGQKAI LFLPMSAKS
```

SEQ ID NO: 2 corresponds to a 17.3 kDa isoform of the human FGF2 protein. SEQ ID NO: 3 corresponds to a 17.1 kDa isoform of the mouse FGF2 protein. SEQ ID NO: 4 corresponds to an 17.3 kDa isoform of the chicken (*Gallus gallus*) FGF2 protein. SEQ ID NO: 5 corresponds to an 17.3 kDa isoform of the short tailed possum (*Monodelphis domestica*) FGF2 protein. SEQ ID NO: 6 corresponds to an 17.3 kDa isoform of the sheep FGF2 protein. SEQ ID NO: 7 corresponds to an 17.3 kDa isoform of the bovine FGF2 protein. SEQ ID NO: 8 corresponds to an 17.1 kDa isoform of the rat FGF2 protein.

Other examples of FGF2 protein include proteins having the following amino acid sequences:

```
                                   (SEQ ID NO: 9)
---------- -MPALPEDGG SG-AFPPGHF KDPKRLYCKN

GGFFLRIHPD GRVDGVREKS DPHIKLQLQA EERGVVSIKG

VCANRYLAMK EDGRLLASKC VTDECFFFER LESNNYNTYR

SRKYTSWYVA LKRTGQYKLG SKTGPGQKAI LFLPMSAKS (SEQ ID NO: 10)
----AAGSIT TLPALPEDGG SG-AFPPGHF KDPKRLYCKN

GGFFLRIHPD GRVDGVREKS DPHIKLQLQA EERGVVSIKG

VCANRYLAMK EDGRLLASKC VTDECFFFER LESNNYNTYR

SRKYTSWYVA LKRTGQYKLG SKTGPGQKAI LFLPMSAKS (SEQ ID NO: 11)
---MAASGIT SLPALPEDGG --AAFPPGHF KDPKRLYCKN

GGFFLRIHPD GRVDGVREKS DPHVKLQLQA EERGVVSIKG

VCANRYLAMK EDGRLLASKC VTEECFFFER LESNNYNTYR

SRKYSSWYVA LKRTGQYKLG SKTGPGQKAI LFLPMSAKS (SEQ ID NO: 12)
---------- -MPALPEDGG --AAFPPGHF KDPKRLYCKN

GGFFLRIHPD GRVDGVREKS DPHVKLQLQA EERGVVSIKG

VCANRYLAMK EDGRLLASKC VTEECFFFER LESNNYNTYR

SRKYSSWYVA LKRTGQYKLG SKTGPGQKAI LFLPMSAKS
```

SEQ ID NOs: 9 and 10 correspond to two recombinant human FGF2 proteins. SEQ ID NO: 11 (Accession: # P15655) corresponds to a recombinant mouse FGF2 protein. SEQ ID NO: 12 corresponds to a recombinant mouse FGF2 protein.

As may be seen in Examples 1 and 11, the mouse protein is able to enhance virus replication in both permissive mouse and permissive human cells, suggesting that corresponding FGF2 proteins from one species would be able to enhance virus replication in permissive cells of another species.

The sequences listed in SEQ ID NOs: 2-12 share the common consensus sequence:

```
                                  (SEQ ID NO: 13)
XXXXXXXXXX XXPXLXXDGG XXXAFPPGHF KDPKRLYCKN

GGFFLRIXPD GRVDGXREKS DPXXKLQLQA EERGVVSIKG

VXANRXLAMK EDGRLLAXKX XTXECFFFER LESNNYNTYR

SRKYXXWYVA LKRTGQYKXG XKTGPGQKAI LFLPMSAKS
``` where each "X" represents a variable residue, and the options for each variable residue is listed in Table 1:

TABLE 1

Variable residues for SEQ ID NO: 13

| Position: | May be: |
|---|---|
| 1 | present or absent, and, if present, may be M |
| 2 | present or absent, and, if present, may be A |
| 3 | present or absent, and, if present, may be A |
| 4 | present or absent, and, if present, may be M or G |
| 5 | present or absent, and, if present, may be A |
| 6 | present or absent, and, if present, may be A |
| 7 | present or absent, and, if present, may be G or S |
| 8 | present or absent, and, if present, may be S or G |
| 9 | present or absent, and, if present, may be I |
| 10 | present or absent, and, if present, may be T |
| 11 | present or absent, and, if present, may be T or S |
| 12 | L or M |
| 14 | A or S |
| 16 | P or S |
| 17 | E, D or G |
| 21 | present or absent, and, if present, may be S or G |
| 22 | present or absent, and, if present, may be G or S |
| 23 | present or absent, and, if present, may be G or A |
| 48 | H or N |
| 56 | V or I |
| 63 | H or N |
| 64 | I or V |
| 82 | C or S |
| 86 | Y or F |
| 98 | S or L |
| 100 | C or Y |
| 101 | V or A |
| 103 | E or D |
| 125 | S or T |
| 126 | S, D or N |
| 139 | L or P |
| 141 | S or P |

It is expected that administering a protein that includes an amino acid sequence according to SEQ ID NO: 13 would also enhance virus replication in permissive cells that expresses a receptor to FGF2 protein.

One specific example of a human recombinant protein, which has been determined to enhance virus replication and, accordingly, may be used according to the present disclosure, is shown in SEQ ID NO: 14 (Accession: # P09038). The portion of the sequence corresponding to SEQ ID NO: 13 is shown in bold.

```
                                  (SEQ ID NO: 14)
MVGVGGGDVE DVTPRPGGCQ ISGRGARGCN GIPGAAAWEA

ALPRRRPRRH PSVNPRSRAA GSPRTRGRRT EERPSGSRLG

DRGRGRALPG GRLGGRGRGR APERVGGRGR GRGTAAPRAA

PAARGSRPGP AGTMAAGSIT TLPALPEDGG SGAFPPGHFK

DPKRLYCKNG GFFLRIHPDG RVDGVREKSD PHIKLQLQAE

ERGVVSIKGV CANRYLAMKE DGRLLASKCV TDECFFFERL
```

-continued
ESNNYNTYRS RKYTSWYVAL KRTGQYKLGS KTGPGQKAIL

FLPMSAKS

As used herein, the term "FGF2 protein" includes any protein that includes a sequence according to any one of SEQ ID NOs: 2-13 and that is able to bind to a receptor for the FGF2 protein.

As used herein, "functional variants of FGF2 protein" are proteins that include a sequence that is at least 90% identical to any one of SEQ ID NOs: 2-12 and that are able to bind to the FGF2 protein receptor. In some examples, the functional variant of FGF2 protein shares at least 95% sequence identity with any one of SEQ ID NOs: 2-12. In yet other examples, the functional variant of FGF2 protein shares at least 98% sequence identity with any one of SEQ ID NOs: 2-12. In particular examples, the functional variant of FGF2 protein shares at least 99% sequence identity with any one of SEQ ID NOs: 2-12.

The percent identities between various exemplary sequences of FGF2 are shown in Table 2. FGF2 amino acid alignments for *Homo sapiens* (NCBI Reference Sequence: EAX05222.1), Pan troglodytes (NCBI Reference Sequence: NP 001103711.1), *Mus musculus* (NCBI Reference Sequence: NP 032032), *Rat norvegicus* (NCBI Reference Sequence: NP 062178.1), *Ovis aries* (NCBI Reference Sequence: NP 001009769.1), *Bos taurus* (NCBI Reference Sequence: NP 776481.1), and *Gallus gallus* (NCBI Reference Sequence: NP 990764.1) were performed using the compositional matrix adjustment method.

TABLE 2

FGF2 protein alignment among multiple species

| Species | Rat norvegicus | Homo sapiens | Pan troglodytes | Ovis aries | Bos taurus | Gallus gallus (SEQ ID NO: 4) |
|---|---|---|---|---|---|---|
| Mus musculus (SEQ ID NO: 3) | 98% (151/154) | 95% (147/155) | 95% (147/155) | 95% (147/155) | 95% (147/155) | 90% (139/154) |
| Rat norvegicus (SEQ ID NO: 8) | | 97% (150/155) | 97% (150/155) | 96% (149/155) | 97% (150/155) | 92% (142/154) |
| Homo sapiens (SEQ ID NO: 2) | | | 100% (155/155) | 98% (152/155) | 99% (154/155) | 92% (142/154) |
| Pan troglodytes | | | | 98% (152/155) | 99% (154/155) | 92% (142/154) |
| Ovis aries (SEQ ID NO: 6) | | | | | 99% (154/155) | 93% (143/154) |
| Bos Taurus (SEQ ID NO: 7) | | | | | | 94% (144/154) |

The variant peptide sequences may include conservative or non-conservative amino acid substitutions. Conservative amino acid substitutions refer to the interchangeability of residues having functionally similar side chains. Conservative substitution tables providing functionally similar amino acids are well known in the art. Table 3 sets forth examples of six groups containing amino acids that are "conservative substitutions" for one another. Other conservative substitution charts are available in the art, and can be used in a similar manner.

TABLE 3

Conservative Substitution Chart

Conservative Substitution Groups

| | |
|---|---|
| 1 | Alanine (A), Serine (S), Threonine (T) |
| 2 | Aspartic Acid (D), Glutamic Acid (E) |

TABLE 3-continued

Conservative Substitution Chart

Conservative Substitution Groups

| | |
|---|---|
| 3 | Asparagine (N), Glutamine (Q) |
| 4 | Arginine (R), Lysine (K) |
| 5 | Isoleucine (I), Leucine (L), Methionine (M), Valine (V) |
| 6 | Phenylalanine (F), Tyrosine (Y), Tryptophan (W) |

Enhanced virus replication when the FGF2 protein or functional variant thereof is administered to the permissive cells should be understood to refer to: (a) the production of a greater number of virus particles by the permissive cells in a given time, (b) an increase in rate of production of virus particles by the permissive cells at a given time, (c) a reduced multiplicity of infection (MOI) needed to produce the same number of virus particles, (d) a reduced MOI needed to produce virus particles at the same rate, or (e) any combination thereof, when compared to identical growth conditions without the FGF2 protein or functional variant thereof being administered to the permissive cell.

For example, enhanced virus replication is seen when 786-0 cells are untreated or pretreated with 20 ng/mL of FGF2 for 24 hours before infection with vesicular stomatitis virus Δ51 (VSVΔ51) at a MOI of 0.01. After 48 hours, cell associated supernatants indicated that the untreated control contained about 1E5 plaque forming units/mL (pfu/mL), while the permissive cells administered FGF2 protein showed enhanced virus replication since about 5E6 pfu/mL were measured.

Figure 2:
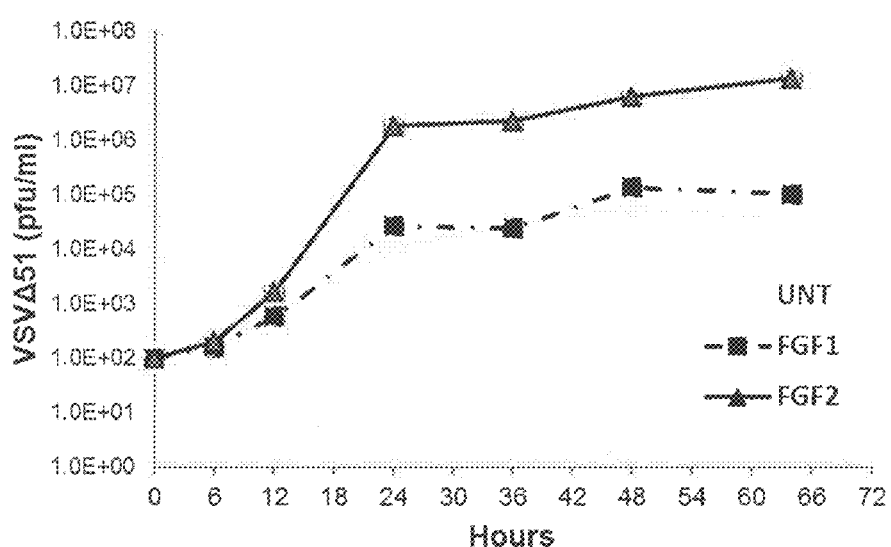
FIG. 2 is a graph illustrating virus replication for untreated, FGF1-treated, and FGF2-treated 786-0 cells over time.

In another example, enhanced virus replication is seen in the increased rate of production of viral particles when 786-0 cells are pre-treated with 20 ng/ml of FGF2 protein 24 hours before infection with vesicular stomatitis virus Δ51 (VSVΔ51) at a MOI of 0.01 and the number of infectious virus particles released by the cells is measured at various time points. After 6 hours, cell associated supernatants indicated that both untreated and FGF2 treated cells contained about 1E2 pfu/ml. After 24 hours, cell associated supernatants indicated that untreated control contained about 1e4 pfu/ml while the 786-0 cells administered FGF2 protein showed enhanced rate of virus replication since about 1e6 pfu/mL were measured. As illustrated in FIG. 2, the rate of production of VSVΔ51 is increased in FGF2-treated 786-0 cells when compared to untreated 786-0 cells.

In a further example, enhanced virus replication is seen when 786-0 cells are untreated or pretreated with 20 ng/mL of FGF2 for 24 hours before infection with vesicular stomatitis virus Δ51 (VSVΔ51) at a MOI of 0.01 or 0.1. After 24 hours, cell associated supernatants indicated that the untreated control infection at a MOI of 0.1 contained about 1e4 plaque forming units/mL (pfu/mL), while the 786-0 cells administered FGF2 protein and infected with 10 fold less virus (MOI of 0.01) contained about 1e5 pfu/mL.

A "permissive cell" or "permissive host" is a term of art that refers to cells or hosts that supports replication of viruses, irrespective of their efficiency to do so. In particular examples, permissive cells have receptors for the virus and an aberrant anti-viral response or an anti-viral response of reduced effectiveness. An anti-viral response of reduced effectiveness may refer to, for example, a lower or a delayed anti-viral response when compared to cells that do not support replication of viruses. One may readily determine whether a cell is permissive with respect to a virus by, for example, administering the virus to the cell and measuring the number of plaque forming units per mL of cell-associated supernatant. In some examples, the cell is considered a permissive cell with respect to that virus if there is greater than 1e4 pfu/mL.

The permissive cells may be, for example, cancer cells, such as adenocarcinoma cells, pancreatic carcinoma cells, ovarian carcinoma cells, renal carcinoma cells, or colon carcinoma cells. Alternatively, the permissive cells may be activated fibroblast cells, such as activated human fetal fibroblast cells or cancer-associated fibroblast cells. Examples of activated human fetal fibroblast cells include WI38 and MRC5 cell.

The virus may be, for example: an oncolytic virus; a live attenuated virus, for example a virus used for live attenuated virus vaccines; or a non-attenuated virus. Examples of viruses that may be used according to the present disclosure include: rhabdovirus (such as vesicular stomatitis virus, VSVΔ51, VSV IFN-β, *maraba virus* or MG1 virus), *vaccinia virus, herpes simplex virus*-1, reovirus, *measles*, Modified *Vaccinia* Ankara virus, Newcastle Disease virus, *influenza virus, West Nile virus, dengue virus*, HIV, rabies virus, *hepatitis virus*, or poliovirus.

Vesicular stomatitis virus (VSV) is a member of the Rhabdovirus family and is classified in the *Vesiculovirus* Genus. VSV has been shown to be a potent oncolytic virus capable of inducing cytotoxicity in many types of human tumour cells in vitro and in vivo (WO 2001/19380).

VSVΔ51 is an engineered attenuated mutant of the natural wild-type isolate of VSV. The Δ51 mutation renders the virus sensitive to IFN signaling via a mutation of the Matrix (M) protein. An exemplary VSVΔ51 is described in WO 2004/085658, which is incorporated herein by reference.

VSV IFN-β is an engineered VSV that includes a polynucleotide sequence encoding interferon-β. An exemplary VSV that encodes interferon-β is described in Jenks N, et al. "Safety studies on intrahepatic or intratumoral injection of oncolytic vesicular stomatitis virus expressing interferon-beta in rodents and nonhuman primates." *Hum Gene Ther*. April 2010; 21(4):451-62, which is incorporated herein by reference.

*Maraba* is another member of the Rhabdovirus family and is also classified in the *Vesiculovirus* Genus. Wild type-*Maraba virus* has also been shown to have a potent oncolytic effect on tumour cells in vitro and in vivo (WO 2009/016433).

MG1 virus is an engineered *maraba virus* that includes a polynucleotide sequence encoding a mutated matrix (M) protein, a polynucleotide sequence encoding a mutated G protein, or both. An exemplary MG1 virus that encodes a mutated M protein and a mutated G protein is described in WO/2011/070440, which is incorporated herein by reference. This MG1 virus is attenuated in normal cells but hypervirulent in cancer cells.

The permissive cells may be cultured cells. Administering the FGF2 protein or functional variant thereof to the permissive cells may include adding to the cell culture a composition that includes the FGF2 protein, or functional variant thereof, and a carrier or diluent. The FGF2 protein or functional variant thereof may be administered to the permissive cells before, after, at the same time, or any combination thereof, that the virus is administered to the permissive cells. When administered to permissive cells that are grown in cell culture, it is desirable to administer the FGF2 protein or functional variant thereof at a concentration greater than or equal to 1 ng/mL. In particular examples, the FGF2 protein or functional variant thereof is administered at a concentration of between 5 ng/mL and 100 ng/mL. In specific examples, the FGF2 protein or functional variant thereof is administered at a concentration of between 20 ng/mL and 50 ng/mL, though higher concentrations would also be expected to result in enhanced virus replication.

Alternatively, or in addition, administering the FGF2 protein of the functional variant thereof to the permissive cells may include adding to the cell culture an oncolytic virus having a genome comprising an open reading frame that encodes the FGF2 protein or functional variant thereof. Permissive cells infected with the virus would produce the FGF2 protein or functional variant thereof. When administered to permissive cells that are grown in cell culture, it is desirable to administer the oncolytic virus at an MOI of at least 0.0005. In particular examples, the cells are more resistant to viral infection and the oncolytic virus is administered at an MOI greater than 0.001. In specific examples, the oncolytic virus is administered at an MOI between 0.01 and 0.1, though higher MOIs would also be expected to result in enhanced virus replication.

The permissive cells may be cancer cells or tumor microenvironment cells in an animal, such as a human being. Administering the FGF2 protein or functional variant thereof and the virus to the permissive cells may include administering an oncolytic virus having a genome comprising an open reading frame that encodes the FGF2 protein or functional variant thereof. Permissive cells infected with the virus would produce the FGF2 protein or functional variant thereof.

When administered to permissive cells that are cancer cells or tumor microenvironment cells in an animal, the amount of oncolytic virus administered to the animal may depend on the oncolytic virus being administered, the mode of administration, the size of the animal. For example, the effective dose for *vaccinia virus* is about 1e9 pfu/human; and the effective dose of a rhabdovirus about 1e11 pfu/human. It may be desirable to administer the oncolytic virus at quantity of a least 1e5 per animal. In particular examples, the oncolytic virus, and other virus of administered, is administered at a quantity between 1e7 and 1e13 pfu/human, though higher pfu's would also be expected to result in enhanced virus replication.

The methods described herein may also include administering to the permissive cells a Type 1 interferon (IFN) scavenger, such as a soluble protein that binds IFN. One example of an IFN scavenger is the *vaccinia virus* B18R protein or functional variant thereof. In one example, the B18R protein has the following amino acid sequence, which corresponds to the B18R protein from the Western Reserve strain of *vaccinia virus* (NCBI Reference Seauence: YP_233082.1):

```
                                            (SEQ ID NO: 15)
MTMKMMVHIY FVSLLLLLFH SYAIDIENEI TEFFNKMRDT

LPAKDSKWLN PACMFGGTMN DIAALGEPFS AKCPPIEDSL

LSHRYKDYVV KWERLEKNRR RQVSNKRVKH GDLWIANYTS

KFSNRRYLCT VTTKNGDCVQ GIVRSHIRKP PSCIPKTYEL

GTHDKYGIDL YCGILYAKHY NNITWYKDNK EINIDDIKYS

QTGKELIIHN PELEDSGRYD CYVHYDDVRI KNDIVVSRCK

ILTVIPSQDH RFKLILDPKI NVTIGEPANI TCTAVSTSLL

IDDVLIEWEN PSGWLIGFDF DVYSVLTSRG GITEATLYFE

NVTEEYIGNT YKCRGHNYYF EKTLTTTVVL E
```

In another example, the B18R protein has the following amino acid sequence, which corresponds to the B18R protein from the Copenhagen strain of *vaccinia virus* (GenBank Accession No: AAA48218.1) and:

```
                                            (SEQ ID NO: 16)
MTMKMMVHIY FVSLSLLLLL FHSYAIDIEN EITEFFNKMR

DTLPAKDSKW LNPACMFGGT MNDMATLGEP FSAKCPPIED

SLLSHRYKDY VVKWERLEKN RRRQVSNKRV KHGDLWIANY

TSKFSNRRYL CTVTTKNGDC VQGIVRSHIK KPPSCIPKTY

ELGTHDKYGI DLYCGILYAK HYNNITWYKD NKEINIDDIK

YSQTGKELII HNPELEDSGR YDCYVHYDDV RIKNDIVVSR

CKILTVIPSQ DHRFKLILDP KINVTIGEPA NITCTAVSTS

LLIDDVLIEW ENPSGWLIGF DFDVYSVLTS RGGITEATLY

FENVTEEYIG NTYKCRGHNY YFEKTLTTTV VLE
```

In yet another example, the B18R protein has the following amino acid sequence, which corresponds to the B18R protein from the Wyeth strain of *vaccinia virus* (GenBank Accession No: AAR18044.1):

```
                                            (SEQ ID NO: 17)
MTMKMMVHIY FVSLSLLLLL FHSYAIDIEN EITEFFNKMR

DTLPAKDSKW LNPACMFGGT MNDMATLGEP FSAKCPPIED

SLLSHRYKDY VVKWERLEKN RRRQVSNKRV KHGDLWIANY

TSKFSNRRYL CTVTTKNGDC VQGIVRSHIR KPPSCIPKTY

ELGTHDKYGI DLYCGILYAK HYNNITWYKD NKEINIDDIK

YSQTGKKLII HNPELEDSGR YDCYVHYDDV RIKNDIVVSR

CKILTVIPSQ DHRFKLKRNC GYASN
```

The B18R protein according to SEQ ID NO: 15 may be encoded by the following nucleotide sequence:

```
                                            (SEQ ID NO: 18)
atgacgatga aaatgatggt acatatatat ttcgtatcat tattgttatt gctattccac agttacgcca tagacatcga aaatgaaatc acagaattct tcaataaaat gagagatact ctaccagcta aagactctaa atggttgaat ccagcatgta tgttcggagg cacaatgaat gatatagccg ctctaggaga gccattcagc gcaaagtgtc ctcctattga agacagtctt ttatcgcaca gatataaaga ctatgtggtt aaatgggaaa ggctagaaaa aaatagacgg cgacaggttt ctaataaacg tgttaaacat ggtgatttat ggatagccaa ctatacatct aaattcagta accgtaggta tttgtgcacc gtaactacaa agaatggtga ctgtgttcag ggtatagtta gatctcatat tagaaaacct ccttcatgca ttccaaaaac atatgaacta ggtactcatg ataagtatgg catagactta tactgtggaa ttctttacgc aaaacattat aataatataa cttggtataa agataataag gaattaata tcgacgacat taagtattca caaacgggaa aggaattaat tattcataat ccagagttag aagatagcgg aagatacgac tgttacgttc attacgacga cgttagaatc aagaatgata tcgtagtatc aagatgtaaa atacttacgg ttataccgtc acaagaccac aggtttaaac taatactaga tccaaaaatc aacgtaacga taggagaacc tgccaatata acatgcactg ctgtgtcaac gtcattattg attgacgatg tactgattga atgggaaaat ccatccggat ggcttatagg attcgatttt gatgtatact ctgttttaac tagtagaggc ggtattaccg aggcgacctt gtactttgaa aatgttactg aagaatatat aggtaataca tataaatgtc gtggacacaa ctattatttt gaaaaaaccc ttacaactac agtagtattg gagtaa.
```

The B18R protein according to SEQ ID NO: 16 may be encoded by the following nucleotide sequence:

```
                                            (SEQ ID NO: 19)
atgacgatga aaatgatggt acatatatat ttcgtatcat tatcattatt gttattgcta ttccacagtt acgccataga catcgaaaat gaaatcacag aattcttcaa taaaatgaga gatactctac cagctaaaga ctctaaatgg ttgaatccag catgtatgtt cggaggcaca atgaatgata tggccactct aggagagcca ttcagtgcaa agtgtcctcc tattgaagac agtctttat cgcacagata taagactat gtggttaaat gggagaggct agaaaagaat agacgcgac aggtttctaa taaacgtgtt aaacatggtg atttatggat agccaactat acatctaaat tcagtaaccg taggtatttg tgcaccgtaa ctacaaagaa tggtgactgt gttcagggta tagttagatc tcatattaaa aaacctcctt catgcattcc aaaaacatat gaactaggta ctcatgataa gtatggcata gacttatact gtggaattct ttacgcaaaa cattataata ataacttg gtataaagat aataaggaaa ttaatatcga cgacattaag
```

-continued

```
tattcacaaa cgggaaagga attaattatt cataatccag agttagaaga tagcggaaga tacgactgtt acgttcatta cgacgacgtt agaatcaaga atgatatcgt agtatcaaga tgtaaaatac ttacggttat accgtcacaa gaccacaggt ttaaactaat actagatccg aaaatcaacg taacgatagg agaacctgcc aatataacat gcactgctgt gtcaacgtca ttattgattg acgatgtact gattgaatgg gaaaatccat ccggatggct tataggattc gattttgatg tatactctgt tttaactagt agaggcggta tcaccgaggc gaccttgtac tttgaaaatg ttactgaaga atatataggt aatacatata aatgtcgtgg acacaactat tattttgaaa aaaccccttac aactacagta gtattggagt aa.
```

The B18R protein according to SEQ ID NO: 17 may be encoded by the following nucleotide sequence:

```
                                    (SEQ ID NO: 20)
atgacgatga aaatgatggt acatatatat ttcgtatcat tatcattatt gttattgcta ttccacagtt acgccataga catcgaaaat gaaatcacag aattcttcaa taaaatgaga gatactctac cagctaaaga ctctaaatgg ttgaatccag catgtatgtt cggaggcaca atgaatgata tagccgctct aggagagcca ttcagcgcaa agtgtcctcc tattgaagac agtctttttat cgcacagata taaagactat gtggttaaat gggaaaggct agaaaagaat agacggcgac aggtttctaa taaacgtgtt aaacatggtg atttatggat agccaactat acatctaaat tcagtaaccg taggtatttg tgcaccgtaa ctacaaagaa tggtgactgt gttcagggta tagttagatc tcatattaga aaacctcctt catgcattcc aaaaacatat gaactaggta ctcatgataa gtatggcata gacttatact gtggaattct ttacgcaaaa cattataata atataacttg gtataaagat aataaggaaa ttaatatcga cgatattaag tattcacaaa cgggaaagaa attaattatt cataatccag agttagaaga tagcggaaga tacgactgtt acgttcatta cgacgacgtt agaatcaaga atgatatcgt agtatcaaga tgtaaaatac ttacggtttt accgtcacaa gaccacaggt ttaaactaaa aagaaattgc ggatatgcgt caaattaa.
```

The IFN scavenger may be administered separately from the FGF2 protein or functional variant thereof, or may be administered at the same time as the FGF2 protein or functional variant thereof. One example of administration at the same time is administration of an oncolytic virus that expresses the IFN scavenger together with the FGF2 protein or functional variant thereof.

The present disclosure also provides an isolated oncolytic virus particle having a genome comprising an open reading frame that encodes FGF2 protein or a functional variant thereof.

The sequence of the FGF2 protein may include an amino acid sequence according to any one of SEQ ID NOs: 2-13. The sequence of the functional variant of the FGF2 protein may, in some examples, include an amino acid sequence that is at least 90% identical to any one of the sequences of SEQ ID NO: 2-12. In particular examples, the sequence of the functional variant of the FGF2 protein may include an amino acid sequence that is at least 95% identical to any one of the sequences of SEQ ID NO: 2-12. In other examples, the sequence of the functional variant of the FGF2 protein may include an amino acid sequence that is at least 98% identical to any one of the sequences of SEQ ID NO: 2-12. In still other examples, the sequence of the functional variant of the FGF2 protein may include an amino acid sequence that is at least 99% identical to any one of the sequences of SEQ ID NO: 2-12.

In particular examples, the oncolytic virus particle has a genome that includes an open reading frame that encodes a protein having an amino acid sequence of at least one of SEQ ID NOs: 2-13.

The FGF2 protein or functional variant thereof may be modified to further include an amino acid sequence of an immunoglobulin signal peptide, such as a peptide that includes the sequence of SEQ ID NO: 1.

The genome of the isolated oncolytic virus may additionally include an open reading frame that encodes an IFN scavenger, such as B18R protein. In particular examples, the B18R protein includes an amino acid sequence according to SEQ ID NO: 15, 16 or 17. The B18R protein may be encoded by, and therefore the genome of the oncolytic virus may include, a DNA sequence according to SEQ ID NO: 18, 19 or 20.

The isolated oncolytic virus particle may be, for example: rhabdovirus (such as vesicular stomatitis virus, VSVΔ51, VSV IFN-β, maraba virus or MG1 virus), vaccinia virus, or herpes simplex virus-1.

EXAMPLES

Methods—Plaque Assay

Virus titers were determined from $10^{-1}$ to $10^{-6}$ dilutions of cell-associated supernatants seeded onto confluent monolayers of Vero cells (Kidney African Green Monkey). At 1 hour post-infection, supernatants were removed and cells were overlayed with 1:1 ratio of 1% agarose:2×DMEM+20% FBS. After 24 hours, cells were fixed for 45 minutes with 3:1 methanol-acetic acid solution. Then, overlayers were removed and fixed cells were stained with 0.2% crystal violet in 20% methanol. Plaques were counted, averaged and multiplied by the dilution factor to determine virus titer as pfu/ml.

Example 1. Enhanced Virus Replication with FGF2 Protein in Different Permissive Cells Lines Single doses of recombinant human fibroblast growth factor 1 (FGF1): 20 ng/mL and recombinant human FGF2: 20 ng/mL were administered to 786-0 cells (human renal-carcinoma), OVCAR8 cells (human ovarian carcinoma), and WI38 cells (human fetal lung fibroblasts) grown in Dubelco's Modified Eagle Medium (DMEM) containing 2-5% fetal bovine serum and 10 mM Hepes for 24 hours before virus infection. WI38 cells are activated fibroblasts, and a human diploid cell line derived from normal embryonic (3 months gestation) lung tissue.

Single doses of mouse FGF1: 20 ng/mL and mouse FGF2: 20 ng/mL were added to wild-type CT26 cells (mouse colon carcinoma) 24 hours before virus infection. The amino acid sequence of the recombinant human FGF2 protein that was used is shown in SEQ ID NO: 9. The amino acid sequence of the recombinant mouse FGF2 protein that was used is shown in SEQ ID NO: 11. Single doses of human FGF1 (20 ng/mL) and FGF2 (20 ng/mL) were also administered to GM38 cells (human normal lung fibroblasts) 24 hours before virus infection. As controls, untreated infected cells were also included for each cell line tested.

FGF1/FGF2 treated or untreated cells were infected with VSVΔ51 virus at an MOI (multiplicity of infection) of 0.01. After 24 hours, cell associated supernatants were collected and the number of infectious virus particles were quantified by plaque assay.

FIG. 1 shows the results for untreated, FGF1-treated, and FGF2-treated VSVΔ51-infected cells. The total number of plaque forming units (PFU)/mL obtained from FGF2-treated cells was at least 15 fold higher that untreated or FGF1-treated cells (786-0, OVCAR8, WI38, and CT26). In contrast, administration of FGF2 did not significantly affect virus replication in normal GM38 fibroblasts, which would not be considered to be permissive cells.

Example 2. Enhanced Virus Replication with FGF2 Protein Over Time

Virus multi-step growth curves were generated in 786-0 cells pre-treated with single doses of human FGF1 (20 ng/ml) or human FGF2 (20 ng/ml). The amino acid sequence of the human FGF2 protein that was used is shown in SEQ ID NO: 9. Untreated infected cells were also included as negative control. After 24 hours, FGF1/FGF2 treated or untreated cells were infected with VSVΔ51 virus at an MOI of 0.01.

Cell associated supernatants containing released virions were collected at various time points (0, 6, 12, 24, 36, 48, and 66 hours post-infection) and the number of infectious virus particles were quantified by plaque assay. FIG. 2 shows the amount of plaque forming units released from untreated, FGF1-treated, and FGF2-treated cells over time.

Example 3. Enhanced Virus Replication at Varying Multiplicities of Infection

A single dose of 20 ng/mL human FGF2 protein was administered to 786-0 cells 24 hours prior to virus infection. The amino acid sequence of the recombinant human FGF2 protein that was used is shown in SEQ ID NO: 9. Control cells were left untreated, or were treated with 20 ng/ml of human FGF1. VSVΔ51 was administered to the cells at MOIs of either 0.1 or 0.01.

Figure 3:
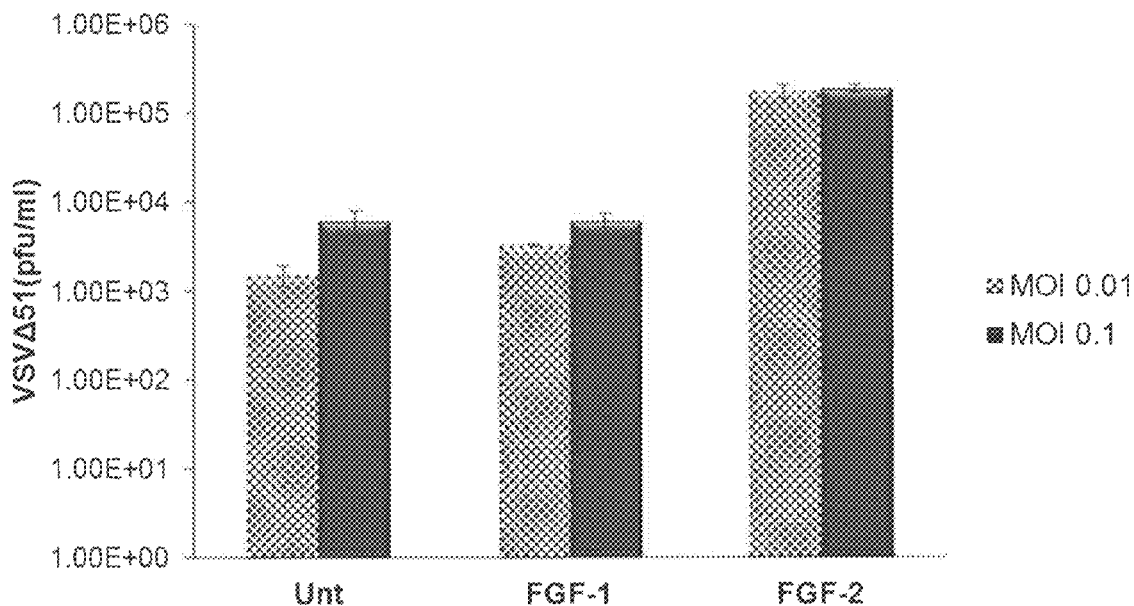
FIG. 3 is a graph illustrating virus replication for untreated, FGF1-treated, and FGF2-treated 786-0 under different multiplicities of infection.

After 24 hours, cell associated supernatants were collected and the number of infectious virus particles were quantified by plaque assay. FIG. 3 shows that FGF2-enhancement of virus replication is independent of the MOIs used and takes place at MOIs as low as 0.01.

Example 4. Dose-Dependent Enhanced Virus Replication

Varying amounts of FGF2 protein were administered to 786-0 cells 24 hours before infection with VSVΔ51 at an MOI of 0.01, resulting in the permissive cells being exposed to FGF2 protein in a range from 20 ng/ml to 500 ng/ml. The amino acid sequence of the recombinant human FGF2 protein that was used is shown in SEQ ID NO: 9.

Figure 4:
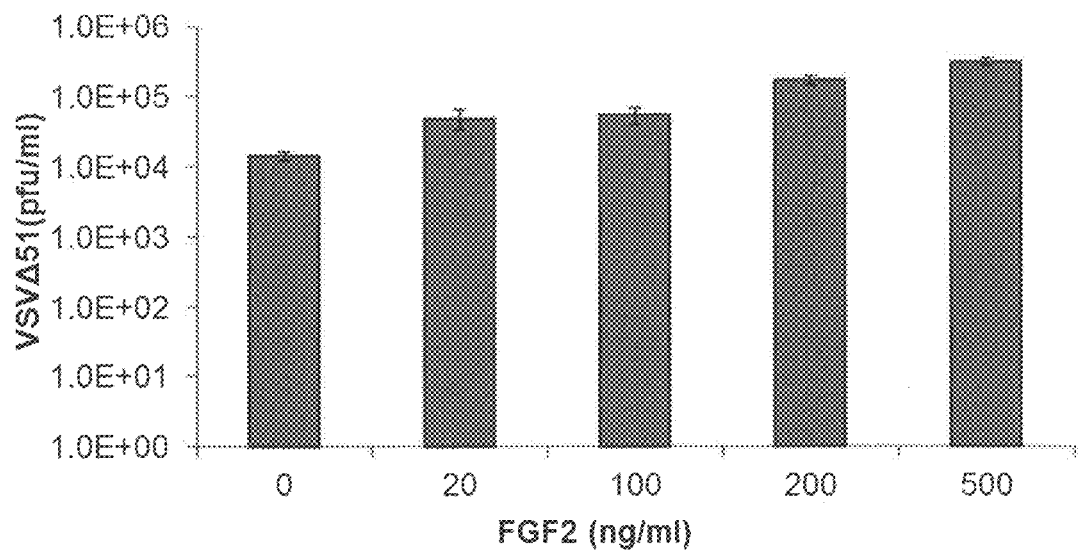
FIG. 4 is a graph illustrating dose-dependent virus replication in 786-0 cells with varying FGF2 concentrations.

After 24 hours, cell associated supernatants were collected and the number of infectious virus particles were quantified by plaque assay. FIG. 4 shows that enhanced VSVΔ51 replication is seen at FGF2 concentrations as low as 20 ng/ml.

Example 5. Reduction of Enhanced Virus Replication with FGF Receptor 1 Inhibitor A single dose of FGF2 recombinant protein (20 ng/ml) and either 50 or 250 nM of FGF Receptor 1 inhibitor (PD173074) were co-administered to 786-0 cells 24 hours prior to virus infection. The amino acid sequence of the recombinant human FGF2 protein that was used is shown in SEQ ID NO: 9. Control cells were left untreated, FGF2-treated, or FGF receptor inhibitor-treated. Untreated or treated cells were infected with VSVΔ51 at MOI of 0.01.

Figure 5:
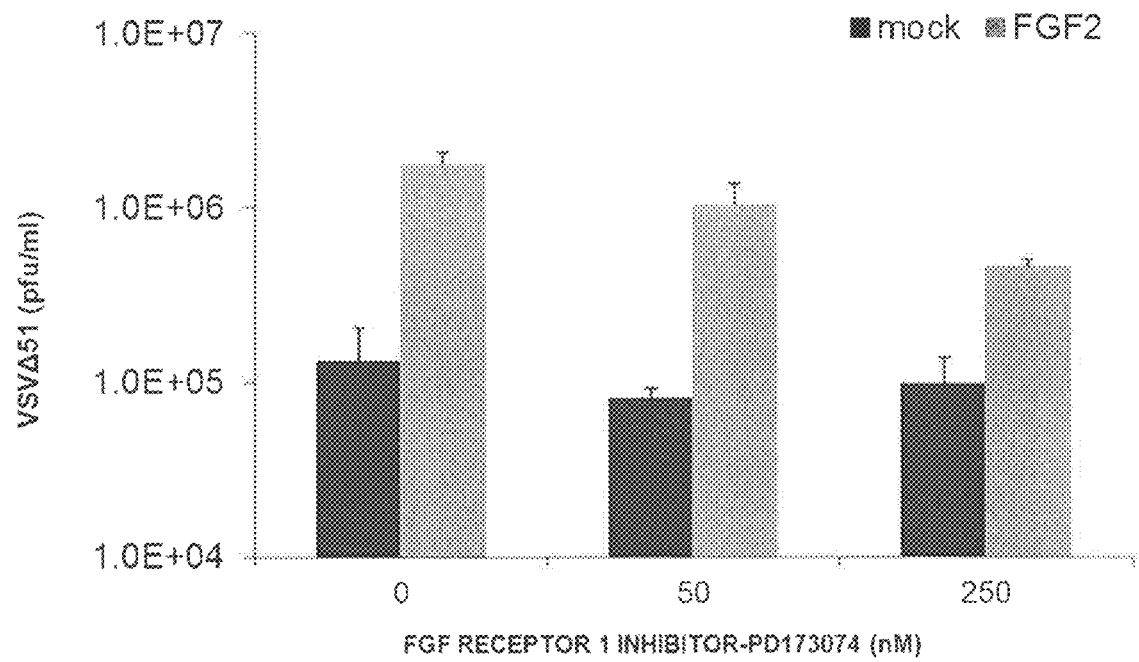
FIG. 5 is a graph illustrating virus replication in untreated and FGF2-treated 786-0 cells with co-administration of FGF Receptor 1 inhibitor.

After 24 hours, cell associated supernatants were collected and the number of infectious virus particles were quantified by plaque assay. FIG. 5 shows that FGF Receptor 1 inhibitor (PD173074) reduces FGF2-induced enhancement of virus replication in 786-0 cells.

Example 6. FGF2 Overcomes Antiviral Responses

FGF2 protein was administered to 786-0 cells at 20 ng/ml for 24 hours prior to infection. The amino acid sequence of the recombinant human FGF2 protein that was used is shown in SEQ ID NO: 9. Controls included FGF1 (20 ng/mL)-treated or untreated cells. The following day increasing amounts of Intron A (IFN-α), ranging from 0 to 50 U/ml, were added to the cells. Four hours post-Intron A administration, cells were infected with VSVΔ51 (MOI: 0.01).

Figure 6:
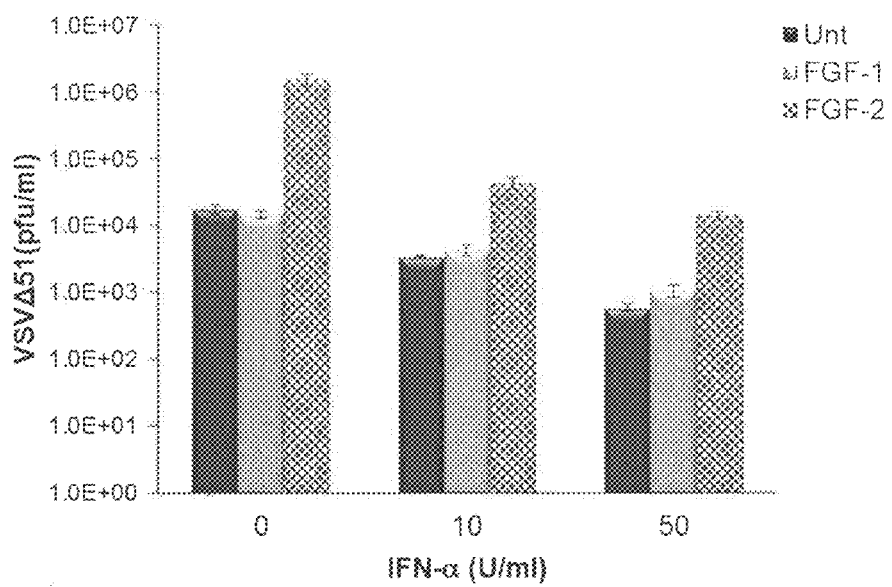
FIG. 6 is a graph illustrating virus replication in untreated, FGF1-treated, and FGF2-treated 786-0 cells in the presence of interferon alpha-2b.

After 24 hours, cell associated supernatants were collected and the number of infectious virus particles were quantified by plaque assay. FIG. 6 shows that even in the presence of Intron A, FGF2-treated cells exhibit higher virus titers (10 fold) compared to control (untreated and FGF1-treated) cells.

Example 7. Enhanced Virus Replication with Different Viruses

Human FGF2 recombinant protein (20 ng/ml) was administered to 786-0 cells 24 hours prior to infection of the cells with various viruses. The amino acid sequence of the recombinant human FGF2 protein that was used is shown in SEQ ID NO: 9. Untreated cells were used as controls during these experiments. VSV (MOI: 0.01), VSVΔ51 (MOI: 0.01), MG1 (MOI: 0.01), JX594-GFP (VV-MOI: 0.01), Reovirus (REOV-MOI: 0.1), or HSV-1 (MOI: 0.05) was administered to the FGF2-treated or untreated cells.

JX594 is a *vaccinia* poxvirus engineered by addition of the GM-CSF gene and deletion of the thymidine kinase gene, which limits viral replication to cells with high levels of thymidine kinase. JX594-GFP is a JX594 virus that encodes the green fluorescent protein as a reporter gene. MG1 virus is a double mutant strain of *Maraba virus* containing both G protein (Q242R) and M protein (L123W) mutations. VSVΔ51 is a mutant strain of VSV containing a deletion of amino acid 51 of its M protein.

After 24 hours, cell associated supernatants from cells infected with VSV, VSVΔ51, and MG1 were collected and the number of infectious virus particles was quantified by plaque assay. In the case of cells infected with JX594-GFP, REOV, or HSV-1, cells and cell-associated supernatants were collected at 48 hours post-infection, and infectious virus particles were titrated by plaque assay.

Titration of HSV-1 encoding GFP was performed following the end-point dilution method ($TCTD_{50}$). Samples were serially diluted from $10^{-1}$ to $10^{-10}$ and inoculated onto confluent monolayers of Vero cells grown in 96 well plates. Samples were titrated in triplicate. Virus-induced cytopathic effect (CPE) was scored 48 hours after infection and the titer was calculated by determining the last dilution giving 50% of wells with cells displaying a CPE.

Titration of REOV was performed in L929 cells (murine fibrosarcoma cell line–1×10$^6$) that were infected with serial dilutions of virus-containing samples in 35 mm dishes for 3 hours. Cells were then washed and overlaid with warm 1% (w/v) agar in culture medium and incubated for 3 days. Viral plaques were visualized by adding neutral red to 0.01% (w/v) final concentration.

To titrate JX-594-GFP, 10-fold serial virus dilutions ranging from $10^{-2}$ to $10^{-7}$ were prepared and inoculated onto confluent monolayers of U2OS cells (Human osteosarcoma cell line). After 2 hours incubation at 37° C., inoculum was removed and cells were overlayed with 1:1 ratio of 3% carboxymethylcellulose:2×DMEM+20% FBS. After 72 hours, cells were fixed and stained for 30 minutes with 0.1% crystal violet in 20% methanol. Plaques were counted, averaged and multiplied by the dilution factor to determine virus titer as pfu/ml.

Figure 7:
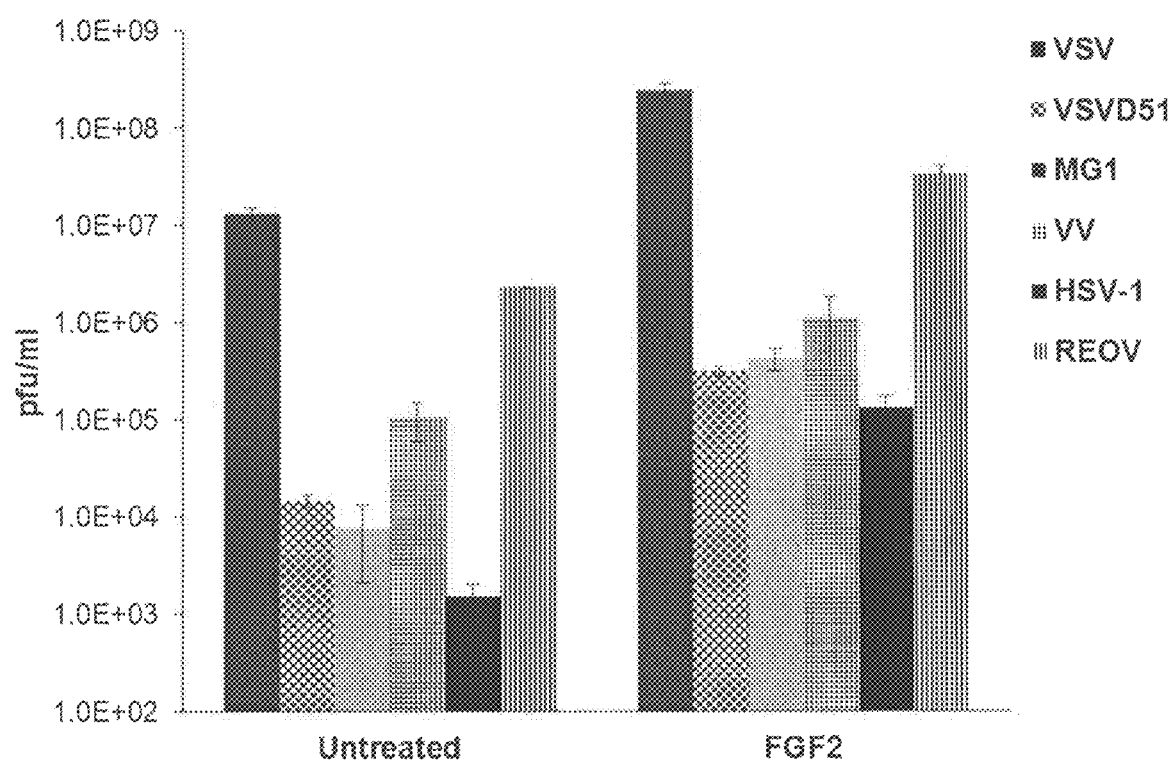
FIG. 7 is a graph illustrating virus replication in untreated and FGF2-treated 786-0 cells with various viruses.

FIG. 7 shows the results for 786-0 cells treated with FGF2 and subsequently infected with VSV, VSVΔ51, MG1, JX594-GFP, REOV, or HSV-1. Pre-treatment of cells with FGF2 resulted in enhanced virus replication for all the tested viruses.

Example 8. Enhanced Virus Replication Ex Vivo 786-0 or MiaPaca tumors were generated in severe combined immunodeficiency (SCID) mice. The tumors were harvested and processed for ex vivo infection as described in Diallo, J., Roy, D., Abdelbary, H., De Silva, N., Bell, J. C. *Ex Vivo Infection of Live Tissue with Oncolytic Viruses*. J. Vis. Exp. (52), e2854, doi:10.3791/2854 (2011).

Human FGF2 protein (100 ng/ml) was added to the tumors 24 hours before virus administration. The amino acid sequence of the recombinant human FGF2 protein that was used is shown in SEQ ID NO: 9. Control tissues were treated with 100 ng/ml of human FGF1 or left untreated. The tissues were infected with 1e5 pfu of VSVΔ51-expressing GFP. After 48 hours, tissue-associated supernatants were harvested and released virus was titrated by plaque assay.

Figure 8:
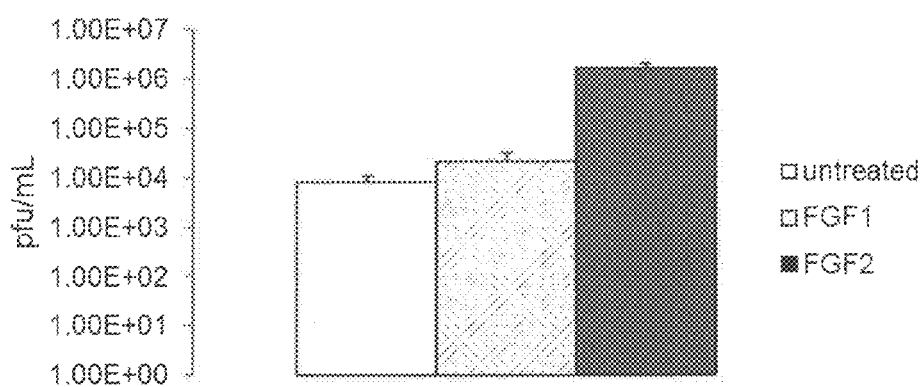
FIG. 8 is a graph illustrating virus replication in untreated, FGF1-treated and FGF2-treated 786-0 tumor cells, where treatment was performed ex-vivo.
Figure 9:
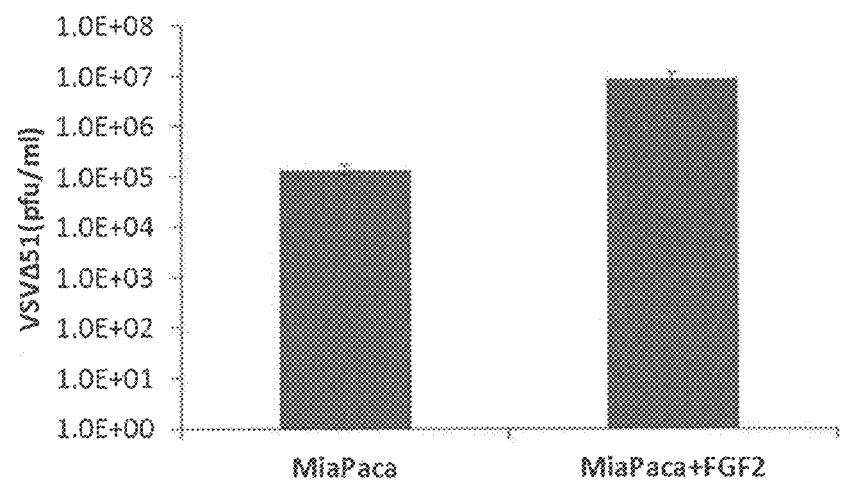
FIG. 9 is a graph illustrating virus replication in untreated, FGF1-treated and FGF2-treated MiaPaca tumor cells, where treatment was performed ex-vivo.

FIG. 8 shows virus titers for 786-0 tumors that were untreated, FGF1-treated, or FGF2-treated, and infected with VSVΔ51 ex vivo. FIG. 9 shows virus titers for MiaPaca tumors that were untreated, FGF1-treated, or FGF2-treated, and infected with VSVΔ51 ex vivo. These figures show an enhancement of ex vivo virus production in tumors pre-treated with FGF2. Representative fluorescent pictures of the tumors show increased ex-vivo virus infection and transgene protein expression (GFP) in tumors pre-treated with FGF2.

Example 9. Enhanced Virus Replication In-Vivo

FGF2 protein was administered to severe combined immunodeficiency (SCID) mice bearing MiaPaca, OVCAR8, or 786-0 subcutaneous tumors by intratumoral injection of 3 μg of human FGF2 protein at 24 hours and at 4 hours before intravenous injection of 1e7 pfu/injection of VSVΔ51. The amino acid sequence of the recombinant human FGF2 protein that was used is shown in SEQ ID NO: 9. PBS was injected as a negative control.

Figure 10:
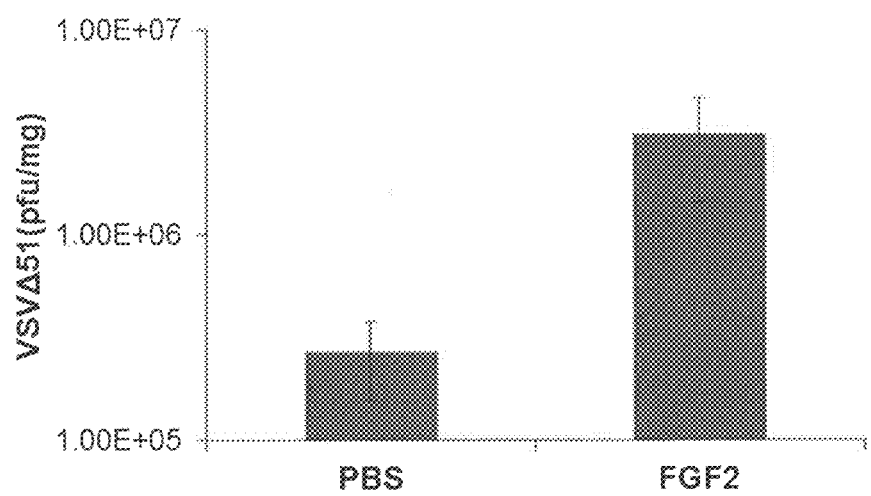
FIG. 10 is a graph illustrating virus replication in untreated and FGF2-treated MiaPaca tumor cells, where treatment was performed in-vivo.
Figure 11:
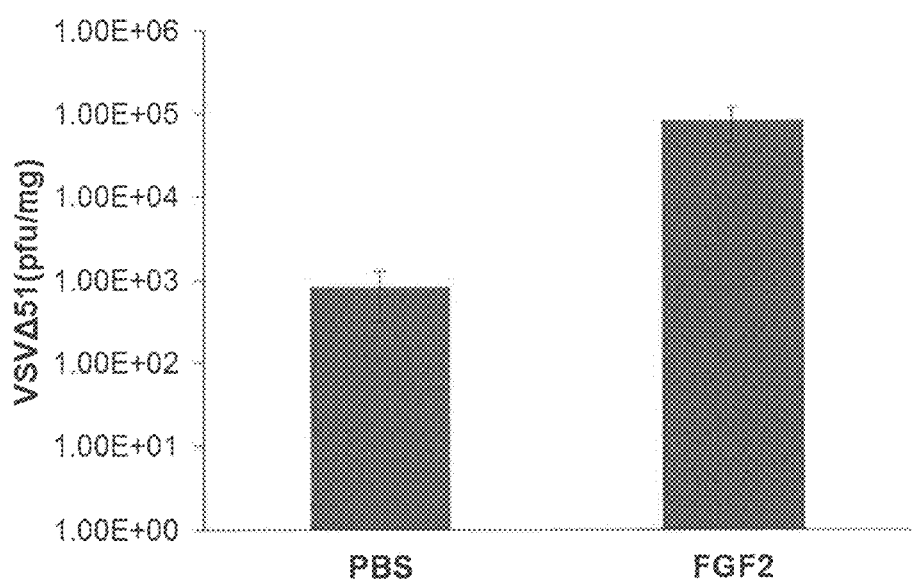
FIG. 11 is a graph illustrating virus replication in untreated and FGF2-treated OVCAR8 tumor cells, where treatment was performed in-vivo.
Figure 12:
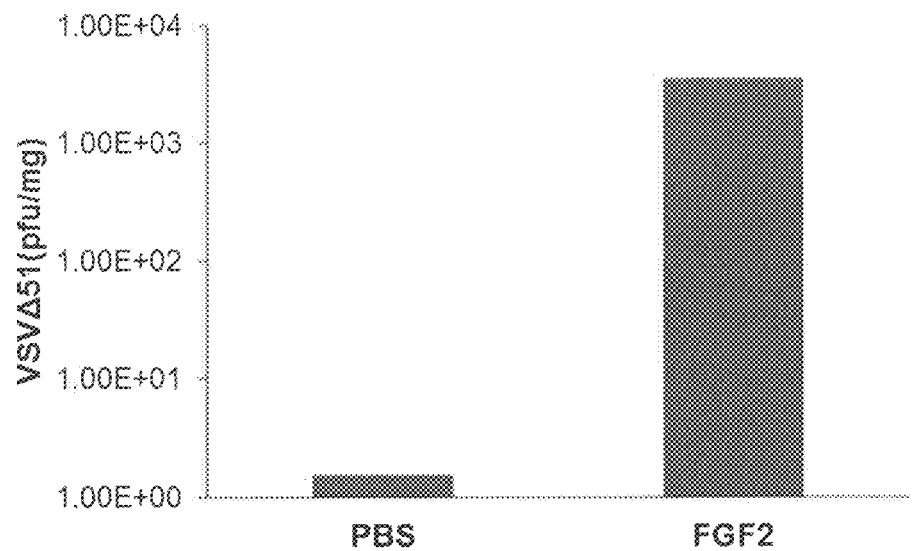
FIG. 12 is a graph illustrating virus replication in untreated and FGF2-treated 786-0 tumor cells, where treatment was performed in-vivo.

FIG. 10 shows titers of VSVΔ51 virus in MiaPaca tumors measured 72 hours post-virus administration by homogenizing the tumors and performing a plaque assay. FIG. 11 shows the VSVΔ51 titration for OVCAR8 tumor, and FIG. 12 shows VSVΔ51 titration for 786-0 tumors. In all cases, injection of FGF2 resulted in enhanced virus replication in in-vivo tumors.

Example 10. Enhanced Virus Replication with Addition of B18R

Recombinant FGF2 protein (20 ng/ml) and B18R (100 ng/ml) protein were co-administered to 786-0 cells and WI38 cells 24 hours and 4 hours before infection. The amino acid sequence of the recombinant human FGF2 protein that was used is shown in SEQ ID NO: 9. The amino acid sequence of the B18R protein was as shown in SEQ ID NO: 15. Controls cells were untreated, single-B18R, or single-FGF2 treated. VSVΔ51 (MOI 0.005) was administered to the treated cells.

Figure 13:
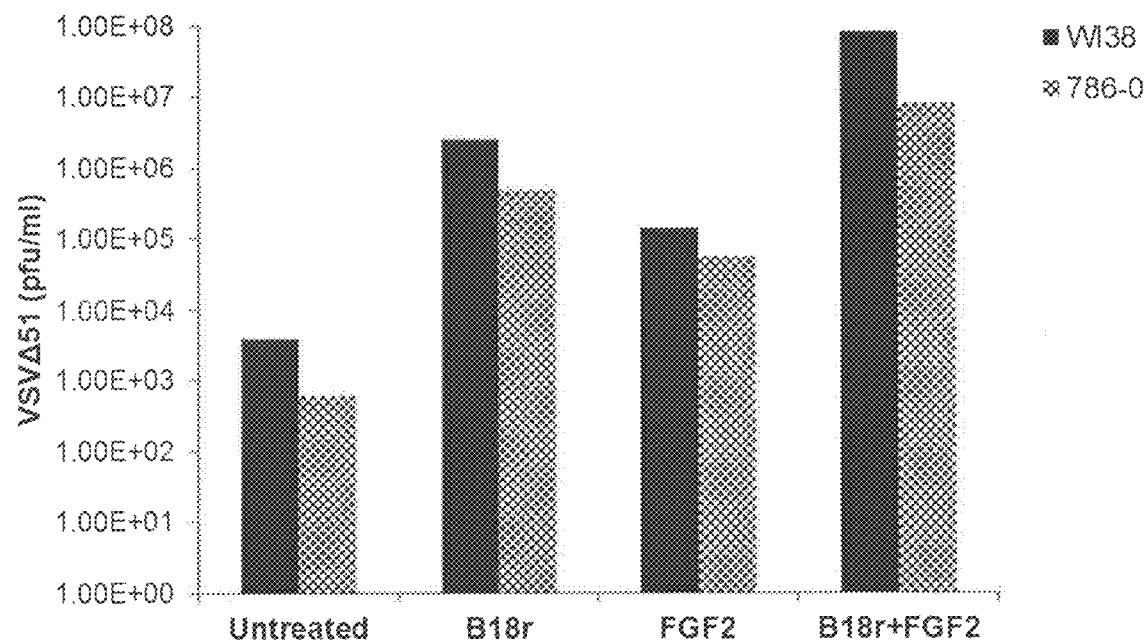
FIG. 13 is a graph illustrating VSVΔ51 replication in cells administered both FGF2 protein and B18R protein.
Figure 14:
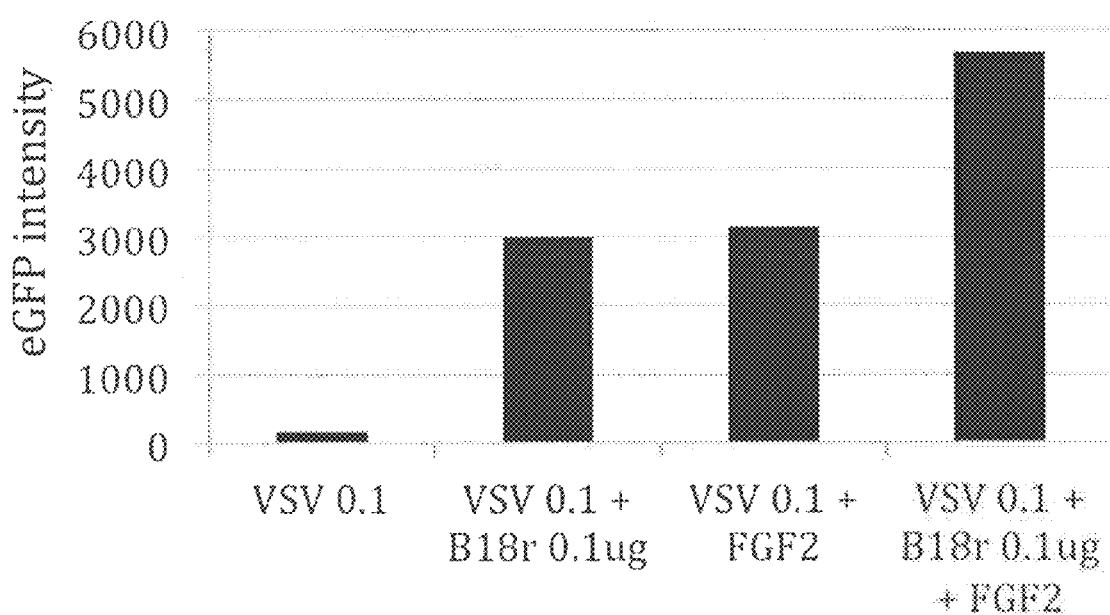
FIG. 14 is a graph illustrating VSVΔ51 replication in cells administered both FGF2 protein and B18R protein.

Twenty-four hours post infection, cell-associated supernatants were collected and the number of infectious virus particles was quantified by plaque assay (FIG. 13) and by GFP fluorescence (FIG. 14). As illustrated in FIGS. 13 and 14, titration results obtained from both 786-0 cells and WI38 fibroblasts show that addition of B18R to FGF2-treated cells further enhances VSVΔ51 virus replication in comparison to the virus-only control, and to the single protein treatment controls.

Recombinant FGF2 protein (20 ng/ml) and B18R (100 ng/ml) protein were co-administered to 786-0 cells 24 hours and 4 hours before infection. The amino acid sequence of the recombinant human FGF2 protein that was used is shown in SEQ ID NO: 9. The amino acid sequence of the B18R protein was as shown in SEQ ID NO: 15. Controls cells were untreated, single-B18R, or single-FGF2 treated. Rhabdovirus MG1-eGFP (MOI 0.001) was administered to the treated cells.

Figure 15:
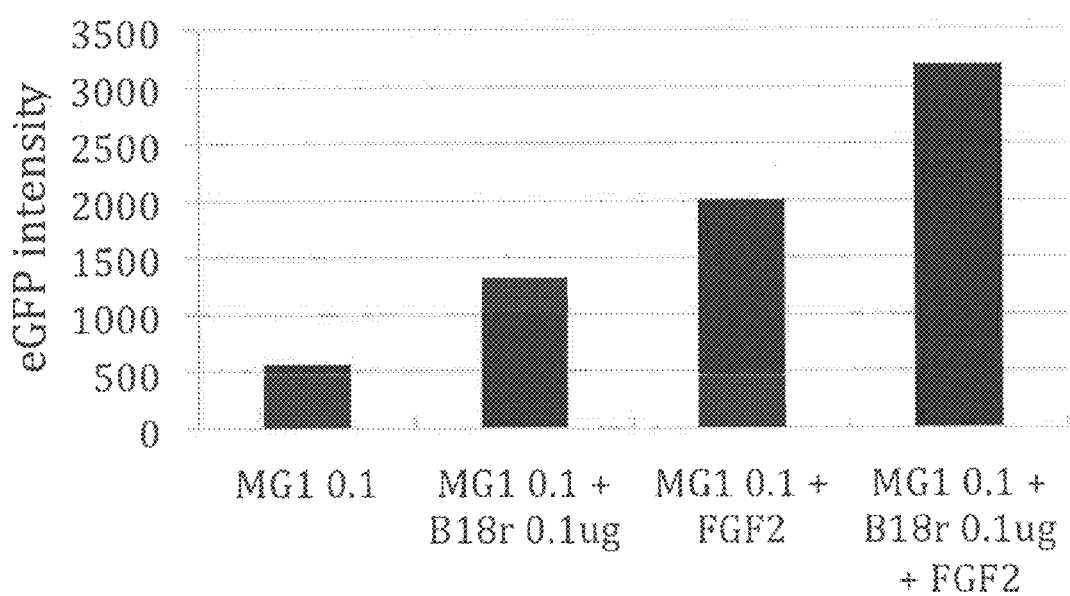
FIG. 15 is a graph illustrating MG1 virus replication in cells administered both FGF2 protein and B18R protein.

Forty-eight hours post infection, GFP pictures were taken and GFP fluorescence was quantified. As illustrated in FIG. 15 fluorescence quantification results show that addition of B18R to FGF2-treated cells further enhances MG1 virus replication in comparison to virus only control or either single protein treatment controls.

Recombinant FGF2 protein (20 ng/ml) and B18R (100 ng/ml) protein were co-administered to 786-0 cells and MRC5 cells 24 hours and 4 hours before infection. The amino acid sequence of the recombinant human FGF2 protein that was used is shown in SEQ ID NO: 9. The amino acid sequence of the B18R protein was as shown in SEQ ID NO: 15. Controls cells were untreated, single-B18R, or single-FGF2 treated. Herpes simple virus (HSV) N212 expressing eGFP (MOI 0.005 for MRC5 cells, MOI 0.01 for 786-0 cells) was administered to the treated cells.

Figure 16:
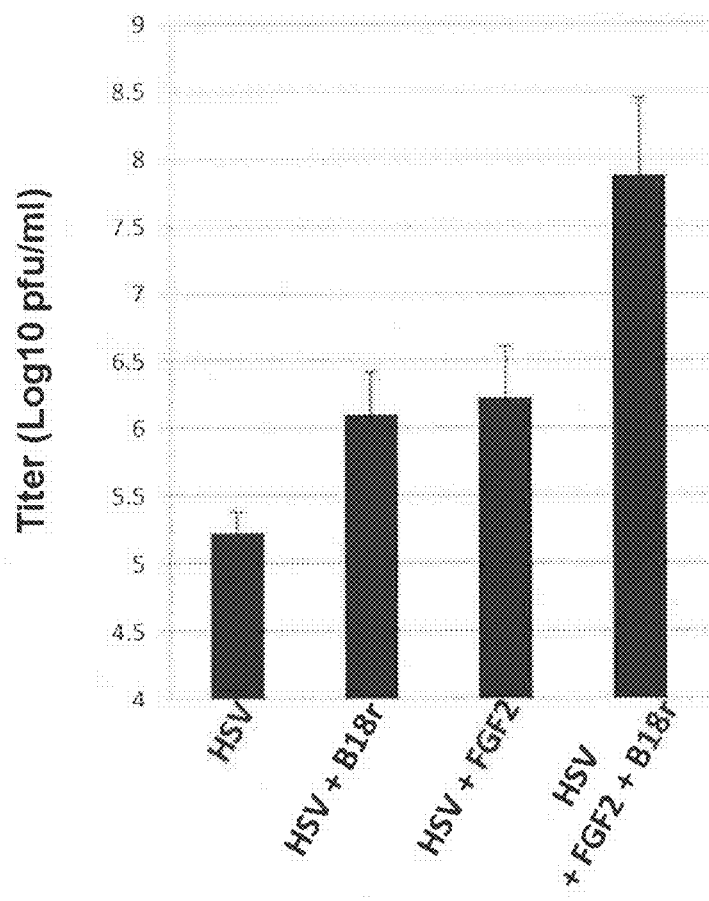
FIG. 16 is a graph illustrating a *herpes simplex virus* replication in cells administered both FGF2 protein and B18R protein.
Figure 17:
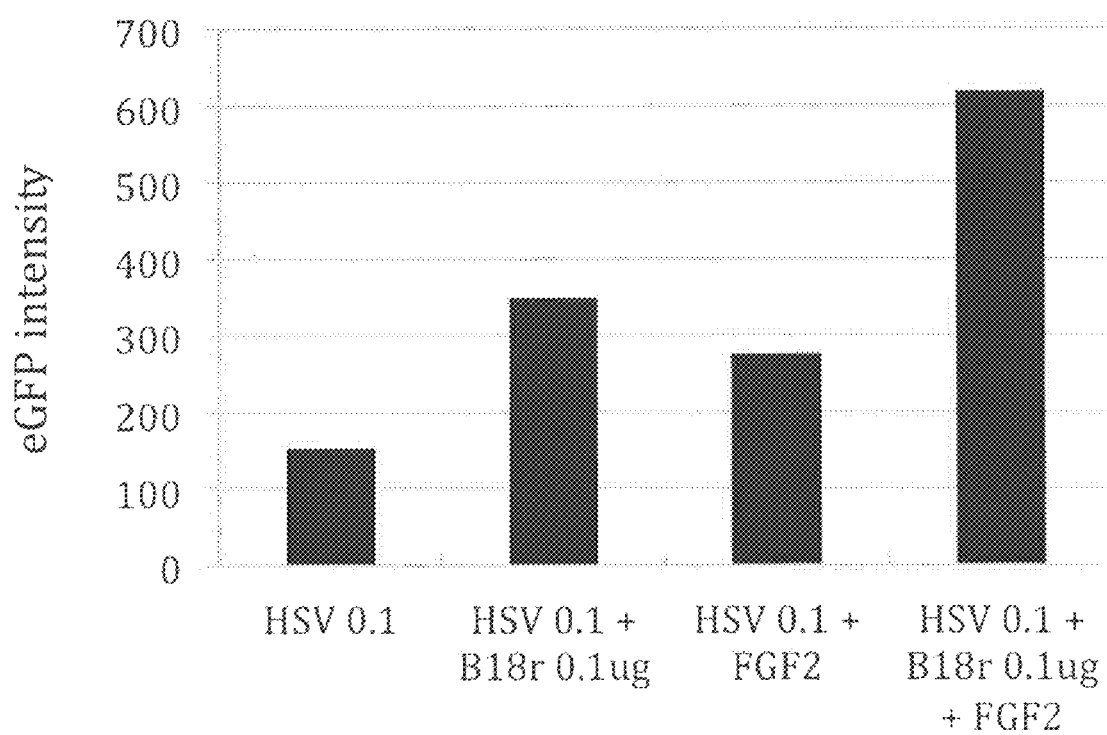
FIG. 17 is a graph illustrating a *herpes simplex virus* replication in cells administered both FGF2 protein and B18R protein.

Forty-eight hours post infection, GFP fluorescence was quantified, cell-associated supernatants were collected and the number of infectious virus particles was quantified by plaque assay. As illustrated in FIGS. 16 and 17, titration results obtained from MRC-5 cells (FIG. 16) and relative fluorescent quantification obtained from 786-0 (FIG. 17) show that addition of B18R to FGF2-treated cells further enhances *herpes simplex virus* replication in comparison to virus only control or either single protein treatment controls.

Recombinant FGF2 protein (20 ng/ml) and B18R (100 ng/ml) protein were co-administered to 786-0 cells 24 hours and 4 hours before infection. The amino acid sequence of the recombinant human FGF2 protein that was used is shown in SEQ ID NO: 9. The amino acid sequence of the B18R protein was as shown in SEQ ID NO: 15. Controls cells were untreated, single-B18R, or single-FGF2 treated. Poxvirus Wyeth thymidine kinase knock-out and expressing eGFP (MOI 0.001) was administered to the treated cells.

Figure 18:
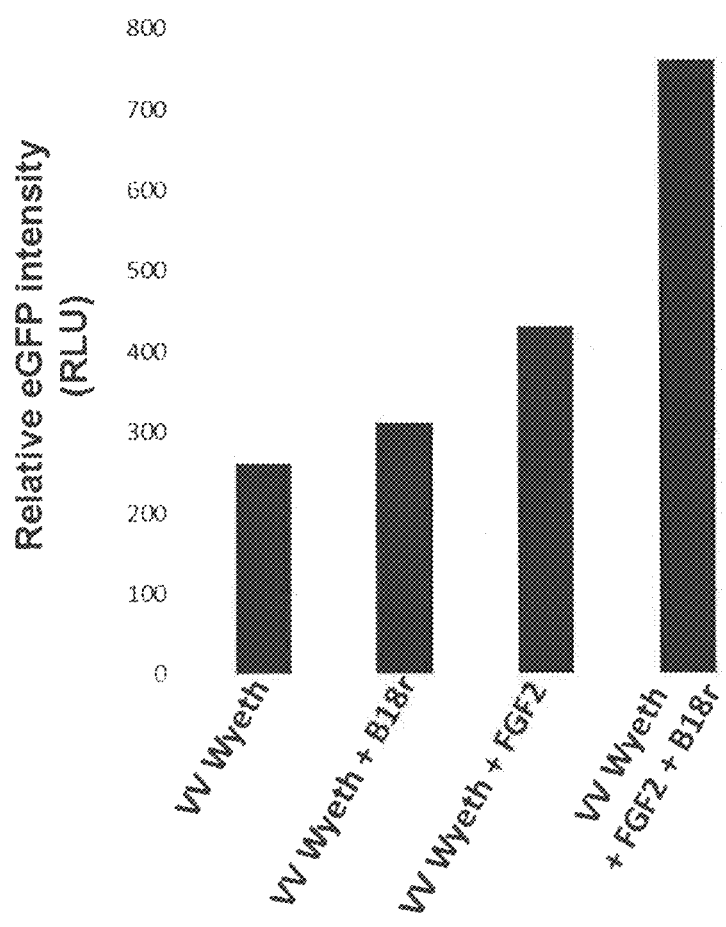
FIG. 18 is a graph illustrating a poxvirus replication in cells administered both FGF2 protein and B18R protein.

Forty-eight hours post infection, GFP fluorescence was quantified. As illustrated in FIG. 18, fluorescence quantification results obtained in 786-0 cells show that addition of B18R to FGF2-treated cells further enhances Poxvirus replication in comparison to virus only control or either single protein treatment controls.

Example 11. Enhanced Virus Replication in Permissive Human Cells Using Mouse FGF2

Mouse FGF2 recombinant protein (20 ng/ml) was administered to 786-0 cells 24 hours prior to infection of the cells with JX594 expressing GFP (MOI: 0.01). Untreated/uninfected cells, and untreated/infected cells, were used as control. After 36 hours of infection, pictures of the cells were taken using a fluorescent microscope.

The relative pixel intensity of GFP expression in uninfected cells (background control), and JX594-GFP infected cells with and without mouse FGF2 protein pre-treatment was calculated using ImageJ software and results are summarized in Table 4. The amino acid sequence of the recombinant murine FGF2 protein that was used is shown in SEQ ID NO: 11. Pre-treatment of human cells with mFGF2 enhances virus replication as denoted by the increase in average relative GFP fluorescent intensity.

TABLE 4

| Condition | Average of pixel intensity* | Relative pixel intensity increase |
| --- | --- | --- |
| Untreated/Uninfected | 5.70 | 1.00 |
| Untreated/JX594-GFP | 13.35 | 2.34 |
| mFGF2/JX594-GFP | 24.90 | 4.37 |

Example 12. Enhance Viral Replication with Recombinant Oncolytic Virus Expressing FGF2 Protein A recombinant MG1 expressing FGF2 protein was cloned and rescued as described previously (European Patent No. 2 064 229 A2, and *Identification of Genetically Modified Maraba Virus as an Oncolytic Rhabdovirus*. Brun et al, Mol. Ther. 2010) with the following modifications: FGF2 open reading frame (GenBank: M17599.1) was cloned at the gene junction between the G and the L protein into a modified LC-Kan vector encoding the viral complementary DNA sequence. To rescue MG1-FGF2 virus, A549 lung carcinoma cells were plated at $3.0 \times 10^5$ cells/well in 6-well plates and were infected 24 hours later with *vaccinia virus* (MOI=10) expressing the T7 RNA polymerase. After 1.5 hour, *vaccinia virus* was removed and cells were co-transfected with LC-KAN Maraba encoding FGF2 (2 μg), and pCI-Neo constructs encoding Maraba N (1 μg), P (1.25 μg), and L (0.25 μg) genes using lipofectamine 2000 (5 μl per well) as per manufacturer's instructions. After 24 hours, medium was replaced with DMEM containing 10% fetal bovine serum. Forty-eight hours post-transfection, medium was collected, filtered (0.2 μm), and 1 ml was used to infect Vero cells. Recombinant virus underwent two rounds of plaque purification (on Vero cells), and was then scaled up, and titrated for further use.

786-0, PANC1 and OVCAR8 cells were infected with MG1 (MOI 0.01) or the recombinant MG1 expressing FGF2 protein (MOI 0.01) for 36 hours. Production of infectious virus particles was quantified by plaque assay in Vero cells. The sequence of the FGF2 expressed by the recombinant MG1 included the sequence of SEQ ID NO: 9. Bright field images were taken 20 hours after infection.

Figure 19:
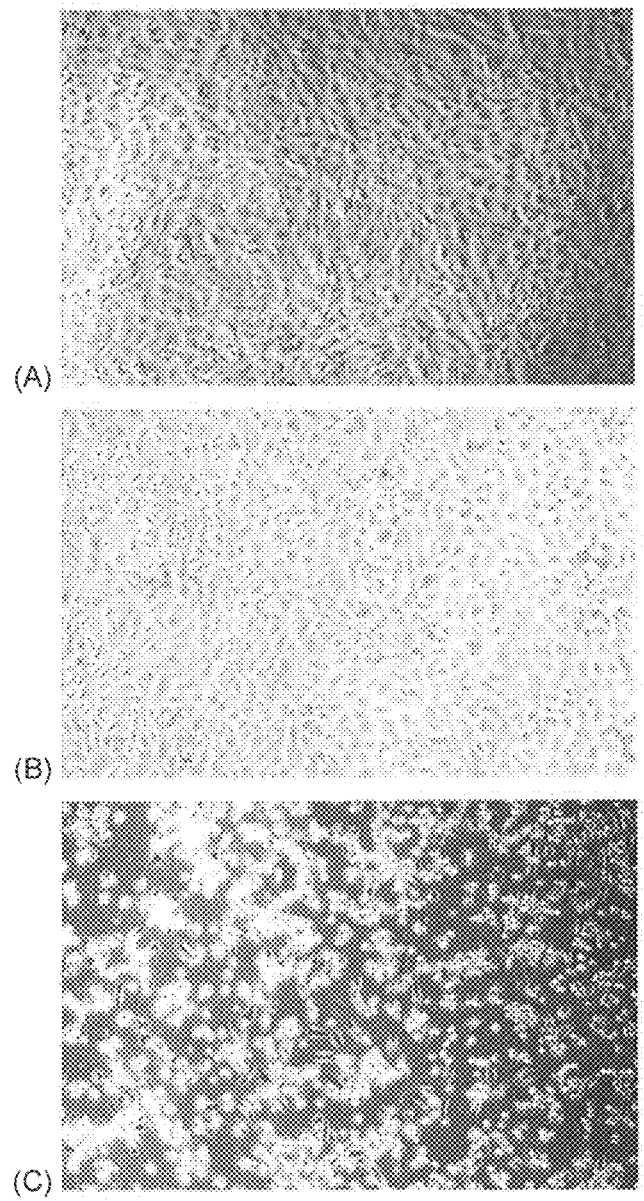
FIG. 19 shows bright-field images of 786-0 cells that were (A) untreated, (B) treated with MG1, and (C) treated with a recombinant MG1 virus expressing FGF2 protein.

FIG. 19 shows images of 786-0 cells that were (A) untreated, (B) treated with MG1, or (C) treated with MG1-FGF2. Treatment with the recombinant MG1-FGF2 virus that expresses FGF2 protein shows increased cell death when compared to the control cells.

Figure 20:
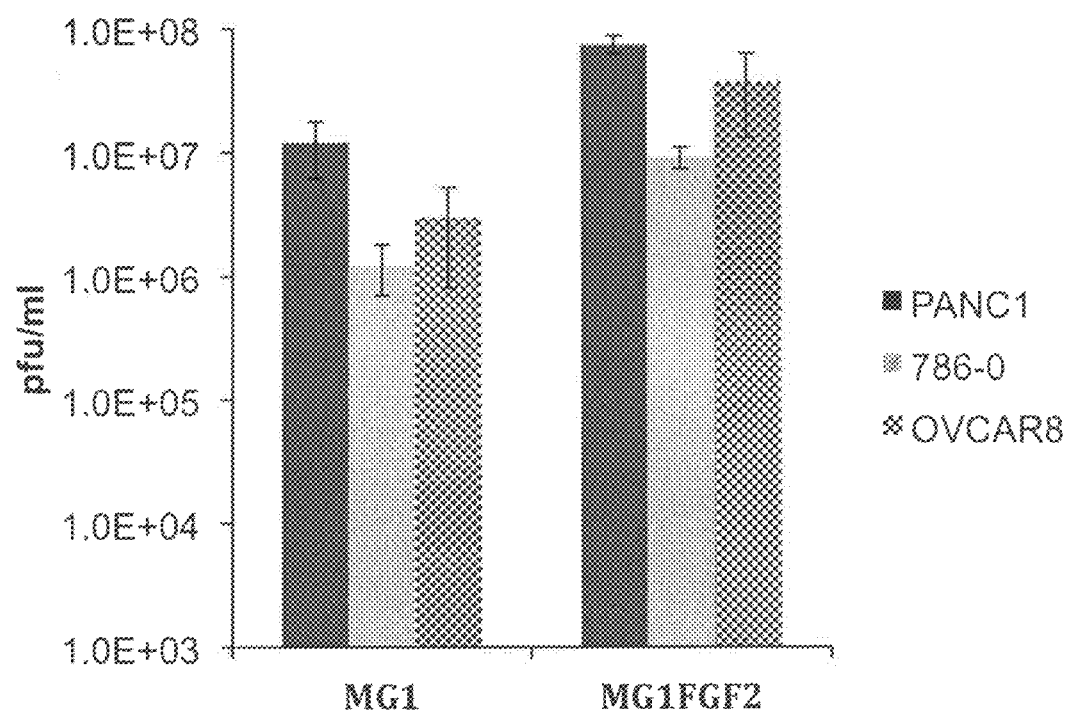
FIG. 20 is a graph showing virus titers from MG1 or MG1-FGF2 infected cells.
Figure 21:
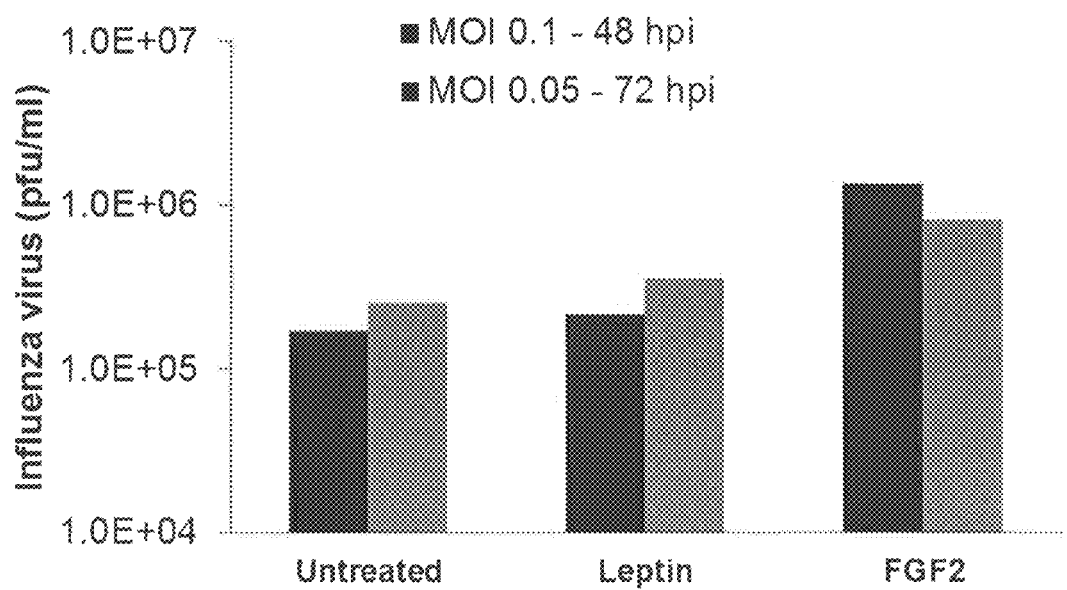
FIG. 21 is a graph illustrating *influenza virus* titers in MRC5 cells treated with either FGF2 or leptin.
Figure 22:
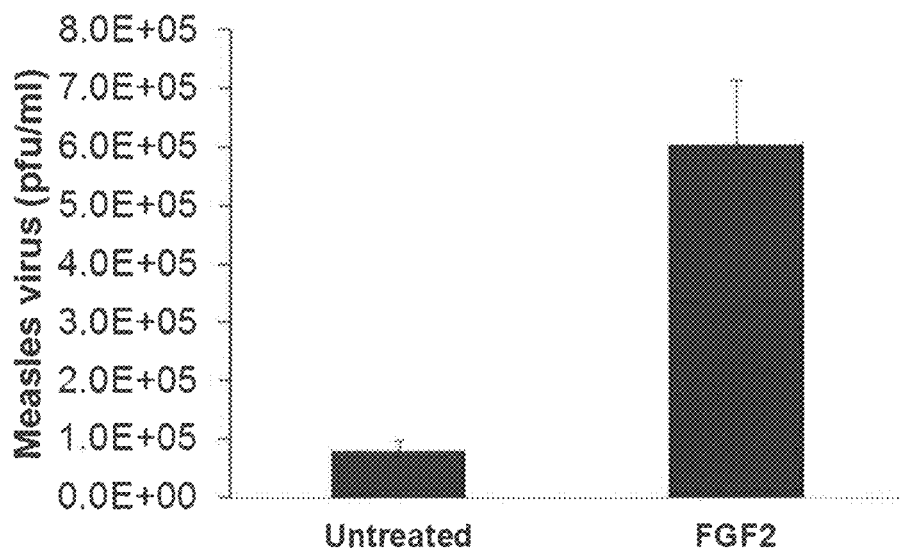
FIG. 22 is a graph showing *measles virus* titers in cells treated with FGF2.

FIG. 20 shows graphs of virus titers from MG1 or MG1-FGF2 infected cells. 786-0, PANC1, OVCAR8 cells were infected with MG1 (MOI 0.01) or MG1-FGF2 (MOI 0.01) for 36 hours, and then production of infectious virus particles was quantified by plaque assay in Vero cells. Recombinant MG1-FGF2 virus that expresses FGF2 protein shows increased virus production when compared to the MG1 virus.

Example 13. Enhanced Viral Replication with *Influenza Virus* in MRC5 Cells Treated with FGF2

MRC5 cells were treated with 100 ng/ml FGF2, 100 ng/ml leptin, or mock treated, in serum free media. The amino acid sequence of the recombinant human FGF2 protein that was used is shown in SEQ ID NO: 9.

48 hours later, cells were infected with the human H1N1 *Influenza A* strain FM/1/47 at MOI 0.05 or 0.1, as indicated, in the presence of 1 μg/ml TPCK trypsin. 48 h (MOI 0.1) or 72 h (MOI 0.05) later, supernatants from triplicate wells were collected and pooled. Viral titers were obtained by ELISA for *Influenza A* nucleoprotein. The resulting titers are illustrated in FIG. 21.

Example 14. Enhanced Viral Replication with Measles Virus in WI38 Cells Treated with FGF2

WI38 cells were treated with 100 ng/ml FGF2, or mock treated, in serum free media. The amino acid sequence of the recombinant human FGF2 protein that was used is shown in SEQ ID NO: 9.

24 hours later, cells were infected with Measles virus (Edmonston strain) at an MOI 0.1. 48 hours later, supernatants were collected and virus titration was performed by plaque assay in Vero cells. The resulting titers are illustrated in FIG. 22.

Example 15. FGF2 is Effective Across Species

Recombinant human FGF2 protein (20 ng/ml) or murine FGF2 (20 ng/ml) protein were administered to MC38 cells (Mouse colon carcinoma) 24 hours before infection. The amino acid sequence of the recombinant human FGF2 protein was as shown in SEQ ID NO: 9. The amino acid sequence of the murine FGF2 protein was as shown in SEQ ID NO: 11. Controls cells were left untreated.

VSVΔ51 (MOI 0.1) was administered to the cells. Forty-eight hours post infection, cell-associated supernatants were collected and the number of infectious virus particles was quantified by plaque assay. As illustrated in Table 5, titration results obtained from MC38 cells show that addition of either human or murine FGF2 enhances virus replication in mouse cells. The data shown are averages of 3 independent experiments and their standard deviations.

TABLE 5

Human and murine FGF2 proteins administered to mouse cells

|  | Untreated/ VSVΔ51 infected | murine FGF2 treated/ VSV Δ51 infected | human FGF2 treated/ VSV Δ51 infected |
|---|---|---|---|
| Virus titre (pfu/mL) | 2.93e6 ± 1.6e5 | 8.20e6 ± 1.1e6 | 7.73e6 ± 9.8e5 |

A single dose of 20 ng/ml murine FGF2 protein was administered to human 768-0 cells 24 hours prior to virus infection. The amino acid sequence of the recombinant murine FGF2 protein was as shown in SEQ ID NO: 11. Control cells were left untreated.

Vaccinia virus encoding the green fluorescent protein (GFP) was administered to the cells at an MOI of 0.01. After 48 hours, infected cells were visualized in a fluorescent microscope and pictures were taken. Average fluorescence pixel intensity associated with expression of GFP (a method to quantify virus replication) was quantified using ImageJ software.

As illustrated in Table 6, fluorescence results show murine FGF2-enhancement of virus replication in a human cell line.

TABLE 6

Murine FGF2 protein administered to human 786-0 cells

|  | Untreated/ Uninfected | Untreated/ JX594-GFP infected | mFGF2 treated/ JX594-GFP infected |
|---|---|---|---|
| Average of pixel intensity | 5.70 | 13.35 | 24.90 |
| Relative pixel intensity increase | 1 | 2.34 | 4.37 |

In the preceding description, for purposes of explanation, numerous details are set forth in order to provide a thorough understanding of the examples. However, it will be apparent to one skilled in the art that these specific details are not required. The above-described examples are intended to be exemplary only. Alterations, modifications and variations can be effected to the particular examples by those of skill in the art without departing from the scope, which is defined solely by the claims appended hereto.

What is claimed is:

1. An isolated oncolytic virus particle having a genome comprising an open reading frame that encodes an FGF2 protein or a functional variant thereof, wherein said FGF2 protein or functional variant thereof further comprises an immunoglobulin signal peptide.

2. The isolated oncolytic virus particle according to claim 1, wherein the amino acid sequence of an immunoglobulin signal peptide comprises the sequence of SEQ ID NO: 1.

3. The isolated oncolytic virus particle according to claim 1, wherein the FGF2 protein comprises an amino acid sequence selected from SEQ ID NOs: 2-13.

4. The isolated oncolytic virus particle according to claim 1, wherein the genome further comprises an open reading frame that encodes a Type 1 interferon scavenger.

5. The isolated oncolytic virus particle according to claim 4, wherein the Type 1 interferon scavenger is a B18R protein.

6. The isolated oncolytic virus particle according to claim 5, wherein the B18R protein comprises an amino acid sequence according to SEQ ID NO: 15, 16, or 17.

7. The isolated oncolytic virus particle according to claim 1, wherein the oncolytic virus is a rhabdovirus, a vaccinia virus, or a herpes simplex virus-1.

8. The isolated oncolytic virus particle according to claim 7, wherein the rhabdovirus is vesicular stomatitis virus, VSVΔ51, VSV INF-β, Maraba virus, or MG1 virus.

9. The isolated oncolytic virus particle according to claim 1, wherein the FGF2 protein comprises an amino acid sequence according to SEQ ID NO: 13.

10. The isolated oncolytic virus particle according to claim 1, wherein the FGF2 protein comprises an amino acid sequence according to SEQ ID NO: 2.

11. The isolated oncolytic virus particle according to claim 5, wherein the B18R protein comprises an amino acid sequence according to SEQ ID NO: 15.

12. The isolated oncolytic virus particle according to claim 1, wherein:
the FGF2 protein comprises an amino acid sequence according to SEQ ID NO: 2; the genome further comprises an open reading frame that encodes a B18R protein that comprises an amino acid sequence according to SEQ ID NO: 15; and the oncolytic virus is a rhabdovirus.

13. The isolated oncolytic virus particle according to claim 12, wherein the rhabdovirus is MG1 virus.

14. The isolated oncolytic virus particle according to claim 12, wherein the rhabdovirus is vesicular stomatitis virus.

* * * * *

SEQUENCE LISTING

<160> NUMBER OF SEQ ID NOS: 20

<210> SEQ ID NO 1
<211> LENGTH: 19
<212> TYPE: PRT
<213> ORGANISM: Mus musculus

<400> SEQUENCE: 1

Met Lys Cys Ser Trp Val Ile Phe Phe Leu Met Ala Val Val Thr Gly
1               5                   10                  15

Val Asn Ser

<210> SEQ ID NO 2
<211> LENGTH: 155
<212> TYPE: PRT
<213> ORGANISM: Homo sapiens

<400> SEQUENCE: 2

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

```
Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155

<210> SEQ ID NO 3
<211> LENGTH: 154
<212> TYPE: PRT
<213> ORGANISM: Mus musculus

<400> SEQUENCE: 3

Met Ala Ala Ser Gly Ile Thr Ser Leu Pro Ala Leu Pro Glu Asp Gly
1               5                   10                  15

Gly Ala Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150

<210> SEQ ID NO 4
<211> LENGTH: 158
<212> TYPE: PRT
<213> ORGANISM: Gallus gallus

<400> SEQUENCE: 4

Met Ala Ala Gly Ala Gly Ser Ile Thr Thr Leu Pro Ala Leu Pro
1               5                   10                  15

Asp Asp Gly Gly Gly Gly Ala Phe Pro Pro Gly His Phe Lys Asp Pro
            20                  25                  30

Lys Arg Leu Tyr Cys Lys Asn Gly Gly Phe Phe Leu Arg Ile Asn Pro
        35                  40                  45

Asp Gly Arg Val Asp Gly Val Arg Glu Lys Ser Asp Pro His Ile Lys
    50                  55                  60

Leu Gln Leu Gln Ala Glu Glu Arg Gly Val Val Ser Ile Lys Gly Val
65                  70                  75                  80

Ser Ala Asn Arg Phe Leu Ala Met Lys Glu Asp Gly Arg Leu Leu Ala
                85                  90                  95

Leu Lys Cys Ala Thr Glu Glu Cys Phe Phe Phe Glu Arg Leu Glu Ser
            100                 105                 110

Asn Asn Tyr Asn Thr Tyr Arg Ser Arg Lys Tyr Ser Asp Trp Tyr Val
        115                 120                 125

Ala Leu Lys Arg Thr Gly Gln Tyr Lys Pro Gly Pro Lys Thr Gly Pro
    130                 135                 140
```

Gly Gln Lys Ala Ile Leu Phe Leu Pro Met Ser Ala Lys Ser
145                 150                 155

<210> SEQ ID NO 5
<211> LENGTH: 156
<212> TYPE: PRT
<213> ORGANISM: Monodelphis domestica

<400> SEQUENCE: 5

Met Ala Ala Gly Ser Ile Thr Thr Leu Pro Ala Leu Ser Gly Asp Gly
1               5                   10                  15

Gly Gly Gly Gly Ala Phe Pro Pro Gly His Phe Lys Asp Pro Lys Arg
                20                  25                  30

Leu Tyr Cys Lys Asn Gly Gly Phe Phe Leu Arg Ile His Pro Asp Gly
            35                  40                  45

Arg Val Asp Gly Ile Arg Glu Lys Ser Asp Pro Asn Ile Lys Leu Gln
        50                  55                  60

Leu Gln Ala Glu Glu Arg Gly Val Val Ser Ile Lys Gly Val Cys Ala
65                  70                  75                  80

Asn Arg Tyr Leu Ala Met Lys Glu Asp Gly Arg Leu Leu Ala Leu Lys
                85                  90                  95

Tyr Val Thr Glu Glu Cys Phe Phe Glu Arg Leu Glu Ser Asn Asn
            100                 105                 110

Tyr Asn Thr Tyr Arg Ser Arg Lys Tyr Ser Asn Trp Tyr Val Ala Leu
        115                 120                 125

Lys Arg Thr Gly Gln Tyr Lys Leu Gly Ser Lys Thr Gly Pro Gly Gln
    130                 135                 140

Lys Ala Ile Leu Phe Leu Pro Met Ser Ala Lys Ser
145                 150                 155

<210> SEQ ID NO 6
<211> LENGTH: 155
<212> TYPE: PRT
<213> ORGANISM: Ovis aries

<400> SEQUENCE: 6

Met Ala Ala Gly Ser Ile Thr Thr Leu Pro Ala Leu Pro Glu Asp Gly
1               5                   10                  15

Gly Ser Ser Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
        50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 7
<211> LENGTH: 155
<212> TYPE: PRT
<213> ORGANISM: Bos taurus

<400> SEQUENCE: 7

Met Ala Ala Gly Ser Ile Thr Thr Leu Pro Ser Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 8
<211> LENGTH: 154
<212> TYPE: PRT
<213> ORGANISM: Rattus norvegicus

<400> SEQUENCE: 8

Met Ala Ala Gly Ser Ile Thr Ser Leu Pro Ala Leu Pro Glu Asp Gly
1               5                   10                  15

Gly Gly Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150

<210> SEQ ID NO 9

<211> LENGTH: 147
<212> TYPE: PRT
<213> ORGANISM: Artificial Sequence
<220> FEATURE:
<223> OTHER INFORMATION: recombinant human protein

<400> SEQUENCE: 9

```
Met Pro Ala Leu Pro Glu Asp Gly Gly Ser Gly Ala Phe Pro Pro Gly
1               5                   10                  15

His Phe Lys Asp Pro Lys Arg Leu Tyr Cys Lys Asn Gly Gly Phe Phe
            20                  25                  30

Leu Arg Ile His Pro Asp Gly Arg Val Asp Gly Val Arg Glu Lys Ser
        35                  40                  45

Asp Pro His Ile Lys Leu Gln Leu Gln Ala Glu Glu Arg Gly Val Val
    50                  55                  60

Ser Ile Lys Gly Val Cys Ala Asn Arg Tyr Leu Ala Met Lys Glu Asp
65                  70                  75                  80

Gly Arg Leu Leu Ala Ser Lys Cys Val Thr Asp Glu Cys Phe Phe Phe
                85                  90                  95

Glu Arg Leu Glu Ser Asn Asn Tyr Asn Thr Tyr Arg Ser Arg Lys Tyr
            100                 105                 110

Thr Ser Trp Tyr Val Ala Leu Lys Arg Thr Gly Gln Tyr Lys Leu Gly
        115                 120                 125

Ser Lys Thr Gly Pro Gly Gln Lys Ala Ile Leu Phe Leu Pro Met Ser
    130                 135                 140

Ala Lys Ser
145
```

<210> SEQ ID NO 10
<211> LENGTH: 154
<212> TYPE: PRT
<213> ORGANISM: Artificial Sequence
<220> FEATURE:
<223> OTHER INFORMATION: recombinant human protein

<400> SEQUENCE: 10

```
Ala Ala Gly Ser Ile Thr Thr Leu Pro Ala Leu Pro Glu Asp Gly Gly
1               5                   10                  15

Ser Gly Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Ile Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Asp Glu Cys Phe Phe Phe Glu Arg Leu Glu Ser Asn Asn Tyr Asn
            100                 105                 110

Thr Tyr Arg Ser Arg Lys Tyr Thr Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150
```

<210> SEQ ID NO 11
<211> LENGTH: 154
<212> TYPE: PRT
<213> ORGANISM: Artificial Sequence
<220> FEATURE:
<223> OTHER INFORMATION: recombinant mouse protein

<400> SEQUENCE: 11

Met Ala Ala Ser Gly Ile Thr Ser Leu Pro Ala Leu Pro Glu Asp Gly
1               5                   10                  15

Gly Ala Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150

<210> SEQ ID NO 12
<211> LENGTH: 146
<212> TYPE: PRT
<213> ORGANISM: Artificial Sequence
<220> FEATURE:
<223> OTHER INFORMATION: recombinant mouse protein

<400> SEQUENCE: 12

Met Pro Ala Leu Pro Glu Asp Gly Gly Ala Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Val Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Glu Glu Cys Phe Phe Phe Glu
                85                  90                  95

Arg Leu Glu Ser Asn Asn Tyr Asn Thr Tyr Arg Ser Arg Lys Tyr Ser
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145

```
<210> SEQ ID NO 13
<211> LENGTH: 159
<212> TYPE: PRT
<213> ORGANISM: Artificial Sequence
<220> FEATURE:
<223> OTHER INFORMATION: Concensus sequence for SEQ ID NO: 2-12
<220> FEATURE:
<221> NAME/KEY: MISC_FEATURE
<222> LOCATION: (1)..(1)
<223> OTHER INFORMATION: Xaa present or absent, and, if present, may be
      Met
<220> FEATURE:
<221> NAME/KEY: MISC_FEATURE
<222> LOCATION: (2)..(2)
<223> OTHER INFORMATION: Xaa present or absent, and, if present, may be
      Ala
<220> FEATURE:
<221> NAME/KEY: MISC_FEATURE
<222> LOCATION: (3)..(3)
<223> OTHER INFORMATION: Xaa present or absent, and, if present, may be
      Ala
<220> FEATURE:
<221> NAME/KEY: MISC_FEATURE
<222> LOCATION: (4)..(4)
<223> OTHER INFORMATION: Xaa present or absent, and, if present, may be
      Met or Gly
<220> FEATURE:
<221> NAME/KEY: MISC_FEATURE
<222> LOCATION: (5)..(5)
<223> OTHER INFORMATION: Xaa present or absent, and, if present, may be
      Ala
<220> FEATURE:
<221> NAME/KEY: MISC_FEATURE
<222> LOCATION: (6)..(6)
<223> OTHER INFORMATION: Xaa present or absent, and, if present, may be
      Ala
<220> FEATURE:
<221> NAME/KEY: MISC_FEATURE
<222> LOCATION: (7)..(7)
<223> OTHER INFORMATION: Xaa present or absent, and, if present, may be
      Gly or Ser
<220> FEATURE:
<221> NAME/KEY: MISC_FEATURE
<222> LOCATION: (8)..(8)
<223> OTHER INFORMATION: Xaa present or absent, and, if present, may be
      Ser or Gly
<220> FEATURE:
<221> NAME/KEY: MISC_FEATURE
<222> LOCATION: (9)..(9)
<223> OTHER INFORMATION: Xaa present or absent, and, if present, may be
      Ile
<220> FEATURE:
<221> NAME/KEY: MISC_FEATURE
<222> LOCATION: (10)..(10)
<223> OTHER INFORMATION: Xaa present or absent, and, if present, may be
      Thr
<220> FEATURE:
<221> NAME/KEY: MISC_FEATURE
<222> LOCATION: (11)..(11)
<223> OTHER INFORMATION: Xaa present or absent, and, if present, may be
      Thr or Ser
<220> FEATURE:
<221> NAME/KEY: MISC_FEATURE
<222> LOCATION: (12)..(12)
<223> OTHER INFORMATION: Xaa may be Leu or Met
<220> FEATURE:
<221> NAME/KEY: MISC_FEATURE
<222> LOCATION: (14)..(14)
<223> OTHER INFORMATION: Xaa may be Ala or Ser
<220> FEATURE:
<221> NAME/KEY: MISC_FEATURE
<222> LOCATION: (16)..(16)
<223> OTHER INFORMATION: Xaa may be Pro or Ser
<220> FEATURE:
<221> NAME/KEY: MISC_FEATURE
<222> LOCATION: (17)..(17)
<223> OTHER INFORMATION: Xaa may be Glu, Asp or Gly
<220> FEATURE:
```

```
<221> NAME/KEY: MISC_FEATURE
<222> LOCATION: (21)..(21)
<223> OTHER INFORMATION: Xaa may be present or absent, and, if present
      may be Ser or Gly
<220> FEATURE:
<221> NAME/KEY: MISC_FEATURE
<222> LOCATION: (22)..(22)
<223> OTHER INFORMATION: Xaa may be present or absent, and, if present,
      may be Gly or Ser
<220> FEATURE:
<221> NAME/KEY: MISC_FEATURE
<222> LOCATION: (23)..(23)
<223> OTHER INFORMATION: Xaa may be present or absent, and, if present,
      may be Gly or Ala
<220> FEATURE:
<221> NAME/KEY: MISC_FEATURE
<222> LOCATION: (48)..(48)
<223> OTHER INFORMATION: Xaa may be His or Asn
<220> FEATURE:
<221> NAME/KEY: MISC_FEATURE
<222> LOCATION: (56)..(56)
<223> OTHER INFORMATION: Xaa may be Val or Ile
<220> FEATURE:
<221> NAME/KEY: MISC_FEATURE
<222> LOCATION: (63)..(63)
<223> OTHER INFORMATION: Xaa may be His or Asn
<220> FEATURE:
<221> NAME/KEY: MISC_FEATURE
<222> LOCATION: (64)..(64)
<223> OTHER INFORMATION: Xaa may be Ile or Val
<220> FEATURE:
<221> NAME/KEY: MISC_FEATURE
<222> LOCATION: (82)..(82)
<223> OTHER INFORMATION: Xaa may be Cys or Ser
<220> FEATURE:
<221> NAME/KEY: MISC_FEATURE
<222> LOCATION: (86)..(86)
<223> OTHER INFORMATION: Xaa may beTyr or Phe
<220> FEATURE:
<221> NAME/KEY: MISC_FEATURE
<222> LOCATION: (98)..(98)
<223> OTHER INFORMATION: Xaa may be Ser or Leu
<220> FEATURE:
<221> NAME/KEY: MISC_FEATURE
<222> LOCATION: (100)..(100)
<223> OTHER INFORMATION: Xaa may be Cys or Tyr
<220> FEATURE:
<221> NAME/KEY: MISC_FEATURE
<222> LOCATION: (101)..(101)
<223> OTHER INFORMATION: Xaa may be Val or Ala
<220> FEATURE:
<221> NAME/KEY: MISC_FEATURE
<222> LOCATION: (103)..(103)
<223> OTHER INFORMATION: Xaa may be Glu or Asp
<220> FEATURE:
<221> NAME/KEY: MISC_FEATURE
<222> LOCATION: (125)..(125)
<223> OTHER INFORMATION: Xaa may be Ser or Thr
<220> FEATURE:
<221> NAME/KEY: MISC_FEATURE
<222> LOCATION: (126)..(126)
<223> OTHER INFORMATION: Xaa may be Ser, Asp or Asn
<220> FEATURE:
<221> NAME/KEY: MISC_FEATURE
<222> LOCATION: (139)..(139)
<223> OTHER INFORMATION: Xaa may be Leu or Pro
<220> FEATURE:
<221> NAME/KEY: MISC_FEATURE
<222> LOCATION: (141)..(141)
<223> OTHER INFORMATION: Xaa may be Ser or Pro

<400> SEQUENCE: 13

Xaa Xaa Xaa Xaa Xaa Xaa Xaa Xaa Xaa Xaa Xaa Xaa Pro Xaa Leu Xaa
1               5                   10                  15

Xaa Asp Gly Gly Xaa Xaa Xaa Ala Phe Pro Pro Gly His Phe Lys Asp
            20                  25                  30
```

```
Pro Lys Arg Leu Tyr Cys Lys Asn Gly Gly Phe Phe Leu Arg Ile Xaa
            35                  40                  45

Pro Asp Gly Arg Val Asp Gly Xaa Arg Glu Lys Ser Asp Pro Xaa Xaa
 50                  55                  60

Lys Leu Gln Leu Gln Ala Glu Glu Arg Gly Val Val Ser Ile Lys Gly
 65                  70                  75                  80

Val Xaa Ala Asn Arg Xaa Leu Ala Met Lys Glu Asp Gly Arg Leu Leu
                 85                  90                  95

Ala Xaa Lys Xaa Xaa Thr Xaa Glu Cys Phe Phe Glu Arg Leu Glu
            100                 105                 110

Ser Asn Asn Tyr Asn Thr Tyr Arg Ser Arg Lys Tyr Xaa Xaa Trp Tyr
            115                 120                 125

Val Ala Leu Lys Arg Thr Gly Gln Tyr Lys Xaa Gly Xaa Lys Thr Gly
            130                 135                 140

Pro Gly Gln Lys Ala Ile Leu Phe Leu Pro Met Ser Ala Lys Ser
145                 150                 155
```

<210> SEQ ID NO 14
<211> LENGTH: 288
<212> TYPE: PRT
<213> ORGANISM: Artificial Sequence
<220> FEATURE:
<223> OTHER INFORMATION: recombinant human protein

<400> SEQUENCE: 14

```
Met Val Gly Val Gly Gly Asp Val Glu Asp Val Thr Pro Arg Pro
 1                   5                  10                  15

Gly Gly Cys Gln Ile Ser Gly Arg Gly Ala Arg Gly Cys Asn Gly Ile
                 20                  25                  30

Pro Gly Ala Ala Ala Trp Glu Ala Ala Leu Pro Arg Arg Arg Pro Arg
            35                  40                  45

Arg His Pro Ser Val Asn Pro Arg Ser Arg Ala Ala Gly Ser Pro Arg
 50                  55                  60

Thr Arg Gly Arg Arg Thr Glu Glu Arg Pro Ser Gly Ser Arg Leu Gly
 65                  70                  75                  80

Asp Arg Gly Arg Gly Arg Ala Leu Pro Gly Gly Arg Leu Gly Gly Arg
                 85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
            115                 120                 125

Gly Pro Ala Gly Thr Met Ala Ala Gly Ser Ile Thr Thr Leu Pro Ala
            130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
            195                 200                 205

Gly Val Cys Ala Asn Arg Tyr Leu Ala Met Lys Glu Asp Gly Arg Leu
            210                 215                 220

Leu Ala Ser Lys Cys Val Thr Asp Glu Cys Phe Phe Phe Glu Arg Leu
225                 230                 235                 240
```

```
Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285

<210> SEQ ID NO 15
<211> LENGTH: 351
<212> TYPE: PRT
<213> ORGANISM: Vaccinia virus

<400> SEQUENCE: 15

Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
                20                  25                  30

Phe Phe Asn Lys Met Arg Asp Thr Leu Pro Ala Lys Asp Ser Lys Trp
            35                  40                  45

Leu Asn Pro Ala Cys Met Phe Gly Gly Thr Met Asn Asp Ile Ala Ala
50                  55                  60

Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95

Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
        115                 120                 125

Cys Thr Val Thr Thr Lys Asn Gly Asp Cys Val Gln Gly Ile Val Arg
    130                 135                 140

Ser His Ile Arg Lys Pro Pro Ser Cys Ile Pro Lys Thr Tyr Glu Leu
145                 150                 155                 160

Gly Thr His Asp Lys Tyr Gly Ile Asp Leu Tyr Cys Gly Ile Leu Tyr
                165                 170                 175

Ala Lys His Tyr Asn Asn Ile Thr Trp Tyr Lys Asp Asn Lys Glu Ile
            180                 185                 190

Asn Ile Asp Asp Ile Lys Tyr Ser Gln Thr Gly Lys Glu Leu Ile Ile
        195                 200                 205

His Asn Pro Glu Leu Glu Asp Ser Gly Arg Tyr Asp Cys Tyr Val His
    210                 215                 220

Tyr Asp Asp Val Arg Ile Lys Asn Asp Ile Val Val Ser Arg Cys Lys
225                 230                 235                 240

Ile Leu Thr Val Ile Pro Ser Gln Asp His Arg Phe Lys Leu Ile Leu
                245                 250                 255

Asp Pro Lys Ile Asn Val Thr Ile Gly Glu Pro Ala Asn Ile Thr Cys
            260                 265                 270

Thr Ala Val Ser Thr Ser Leu Leu Ile Asp Asp Val Leu Ile Glu Trp
        275                 280                 285

Glu Asn Pro Ser Gly Trp Leu Ile Gly Phe Asp Phe Asp Val Tyr Ser
    290                 295                 300

Val Leu Thr Ser Arg Gly Gly Ile Thr Glu Ala Thr Leu Tyr Phe Glu
305                 310                 315                 320

Asn Val Thr Glu Glu Tyr Ile Gly Asn Thr Tyr Lys Cys Arg Gly His
                325                 330                 335
```

```
Asn Tyr Tyr Phe Glu Lys Thr Leu Thr Thr Thr Val Val Leu Glu
            340                 345                 350

<210> SEQ ID NO 16
<211> LENGTH: 353
<212> TYPE: PRT
<213> ORGANISM: Vaccinia virus

<400> SEQUENCE: 16

Met Thr Met Lys Met Met Val His Ile Tyr Phe Val Ser Leu Ser Leu
1               5                   10                  15

Leu Leu Leu Leu Phe His Ser Tyr Ala Ile Asp Ile Glu Asn Glu Ile
            20                  25                  30

Thr Glu Phe Phe Asn Lys Met Arg Asp Thr Leu Pro Ala Lys Asp Ser
        35                  40                  45

Lys Trp Leu Asn Pro Ala Cys Met Phe Gly Gly Thr Met Asn Asp Met
50                  55                  60

Ala Thr Leu Gly Glu Pro Phe Ser Ala Lys Cys Pro Pro Ile Glu Asp
65                  70                  75                  80

Ser Leu Leu Ser His Arg Tyr Lys Asp Tyr Val Val Lys Trp Glu Arg
                85                  90                  95

Leu Glu Lys Asn Arg Arg Arg Gln Val Ser Asn Lys Arg Val Lys His
            100                 105                 110

Gly Asp Leu Trp Ile Ala Asn Tyr Thr Ser Lys Phe Ser Asn Arg Arg
        115                 120                 125

Tyr Leu Cys Thr Val Thr Thr Lys Asn Gly Asp Cys Val Gln Gly Ile
130                 135                 140

Val Arg Ser His Ile Lys Lys Pro Pro Ser Cys Ile Pro Lys Thr Tyr
145                 150                 155                 160

Glu Leu Gly Thr His Asp Lys Tyr Gly Ile Asp Leu Tyr Cys Gly Ile
                165                 170                 175

Leu Tyr Ala Lys His Tyr Asn Asn Ile Thr Trp Tyr Lys Asp Asn Lys
            180                 185                 190

Glu Ile Asn Ile Asp Asp Ile Lys Tyr Ser Gln Thr Gly Lys Glu Leu
        195                 200                 205

Ile Ile His Asn Pro Glu Leu Glu Asp Ser Gly Arg Tyr Asp Cys Tyr
210                 215                 220

Val His Tyr Asp Asp Val Arg Ile Lys Asn Asp Ile Val Val Ser Arg
225                 230                 235                 240

Cys Lys Ile Leu Thr Val Ile Pro Ser Gln Asp His Arg Phe Lys Leu
                245                 250                 255

Ile Leu Asp Pro Lys Ile Asn Val Thr Ile Gly Glu Pro Ala Asn Ile
            260                 265                 270

Thr Cys Thr Ala Val Ser Thr Ser Leu Leu Ile Asp Asp Val Leu Ile
        275                 280                 285

Glu Trp Glu Asn Pro Ser Gly Trp Leu Ile Gly Phe Asp Phe Asp Val
290                 295                 300

Tyr Ser Val Leu Thr Ser Arg Gly Gly Ile Thr Glu Ala Thr Leu Tyr
305                 310                 315                 320

Phe Glu Asn Val Thr Glu Glu Tyr Ile Gly Asn Thr Tyr Lys Cys Arg
                325                 330                 335

Gly His Asn Tyr Tyr Phe Glu Lys Thr Leu Thr Thr Thr Val Val Leu
            340                 345                 350

Glu
```

<210> SEQ ID NO 17
<211> LENGTH: 265
<212> TYPE: PRT
<213> ORGANISM: Vaccinia virus

<400> SEQUENCE: 17

```
Met Thr Met Lys Met Met Val His Ile Tyr Phe Val Ser Leu Ser Leu
1               5                   10                  15

Leu Leu Leu Leu Phe His Ser Tyr Ala Ile Asp Ile Glu Asn Glu Ile
            20                  25                  30

Thr Glu Phe Phe Asn Lys Met Arg Asp Thr Leu Pro Ala Lys Asp Ser
        35                  40                  45

Lys Trp Leu Asn Pro Ala Cys Met Phe Gly Gly Thr Met Asn Asp Met
50                  55                  60

Ala Thr Leu Gly Glu Pro Phe Ser Ala Lys Cys Pro Pro Ile Glu Asp
65                  70                  75                  80

Ser Leu Leu Ser His Arg Tyr Lys Asp Tyr Val Val Lys Trp Glu Arg
                85                  90                  95

Leu Glu Lys Asn Arg Arg Arg Gln Val Ser Asn Lys Arg Val Lys His
            100                 105                 110

Gly Asp Leu Trp Ile Ala Asn Tyr Thr Ser Lys Phe Ser Asn Arg Arg
        115                 120                 125

Tyr Leu Cys Thr Val Thr Thr Lys Asn Gly Asp Cys Val Gln Gly Ile
130                 135                 140

Val Arg Ser His Ile Arg Lys Pro Pro Ser Cys Ile Pro Lys Thr Tyr
145                 150                 155                 160

Glu Leu Gly Thr His Asp Lys Tyr Gly Ile Asp Leu Tyr Cys Gly Ile
                165                 170                 175

Leu Tyr Ala Lys His Tyr Asn Asn Ile Thr Trp Tyr Lys Asp Asn Lys
            180                 185                 190

Glu Ile Asn Ile Asp Asp Ile Lys Tyr Ser Gln Thr Gly Lys Lys Leu
        195                 200                 205

Ile Ile His Asn Pro Glu Leu Glu Asp Ser Gly Arg Tyr Asp Cys Tyr
210                 215                 220

Val His Tyr Asp Asp Val Arg Ile Lys Asn Asp Ile Val Val Ser Arg
225                 230                 235                 240

Cys Lys Ile Leu Thr Val Ile Pro Ser Gln Asp His Arg Phe Lys Leu
                245                 250                 255

Lys Arg Asn Cys Gly Tyr Ala Ser Asn
            260                 265
```

<210> SEQ ID NO 18
<211> LENGTH: 1056
<212> TYPE: DNA
<213> ORGANISM: Vaccinia virus

<400> SEQUENCE: 18

| | |
|---|---|
| atgacgatga aaatgatggt acatatatat ttcgtatcat tattgttatt gctattccac | 60 |
| agttacgcca tagacatcga aaatgaaatc acagaattct tcaataaaat gagagatact | 120 |
| ctaccagcta aagactctaa atggttgaat ccagcatgta tgttcggagg cacaatgaat | 180 |
| gatatagccg ctctaggaga gccattcagc gcaaagtgtc ctcctattga agacagtctt | 240 |
| ttatcgcaca gatataaaga ctatgtggtt aaatgggaaa ggctagaaaa aaatagacgg | 300 |
| cgacaggttt ctaataaacg tgttaaacat ggtgatttat ggatagccaa ctatacatct | 360 |

-continued

```
aaattcagta accgtaggta tttgtgcacc gtaactacaa agaatggtga ctgtgttcag      420
ggtatagtta gatctcatat tagaaaacct ccttcatgca ttccaaaaac atatgaacta      480
ggtactcatg ataagtatgg catagactta tactgtggaa ttctttacgc aaaacattat      540
aataatataa cttggtataa agataataag gaaattaata tcgacgacat taagtattca     600
caaacgggaa aggaattaat tattcataat ccagagttag aagatagcgg aagatacgac      660
tgttacgttc attacgacga cgttagaatc aagaatgata tcgtagtatc aagatgtaaa      720
atacttacgg ttataccgtc acaagaccac aggtttaaac taatactaga tccaaaaatc      780
aacgtaacga taggagaacc tgccaatata acatgcactg ctgtgtcaac gtcattattg      840
attgacgatg tactgattga atgggaaaat ccatccggat ggcttatagg attcgatttt      900
gatgtatact ctgttttaac tagtagaggc ggtattaccg aggcgacctt gtactttgaa      960
aatgttactg aagaatatat aggtaataca tataaatgtc gtggacacaa ctattatttt     1020 gaaaaaccc ttacaactac agtagtattg gagtaa                               1056
```

<210> SEQ ID NO 19
<211> LENGTH: 1062
<212> TYPE: DNA
<213> ORGANISM: Vaccinia virus

<400> SEQUENCE: 19

```
atgacgatga aaatgatggt acatatatat ttcgtatcat tatcattatt gttattgcta      60
ttccacagtt acgccataga catcgaaaat gaaatcacag aattcttcaa taaaatgaga     120
gatactctac cagctaaaga ctctaaatgg ttgaatccag catgtatgtt cggaggcaca     180
atgaatgata tggccactct aggagagcca ttcagtgcaa agtgtcctcc tattgaagac     240
agtcttttat cgcacagata taagactat gtggttaaat gggagaggct agaaaagaat      300
agacggcgac aggtttctaa taacgtgtt aaacatggtg atttatggat agccaactat      360
acatctaaat tcagtaaccg taggtatttg tgcaccgtaa ctacaaagaa tggtgactgt     420
gttcagggta tagttagatc tcatattaaa aaacctcctt catgcattcc aaaaacatat     480
gaactaggta ctcatgataa gtatggcata gacttatact gtggaattct ttacgcaaaa     540
cattataata atataacttg gtataaagat aataaggaaa ttaatatcga cgacattaag     600
tattcacaaa cgggaaagga attaattatt cataatccag agttagaaga tagcggaaga      660
tacgactgtt acgttcatta cgacgacgtt agaatcaaga atgatatcgt agtatcaaga     720
tgtaaaatac ttacggttat accgtcacaa gaccacaggt ttaaactaat actagatccg     780
aaaatcaacg taacgatagg agaacctgcc aatataacat gcactgctgt gtcaacgtca      840
ttattgattg acgatgtact gattgaatgg aaaatccat ccggatggct tataggattc     900
gattttgatg tatactctgt tttaactagt agaggcggta tcaccgaggc gaccttgtac     960
tttgaaaatg ttactgaaga atatataggt aatacatata aatgtcgtgg acacaactat     1020
tattttgaaa aaaccttac aactacagta gtattggagt aa                         1062
```

<210> SEQ ID NO 20
<211> LENGTH: 798
<212> TYPE: DNA
<213> ORGANISM: Vaccinia virus

<400> SEQUENCE: 20

```
atgacgatga aaatgatggt acatatatat ttcgtatcat tatcattatt gttattgcta      60
```

```
ttccacagtt acgccataga catcgaaaat gaaatcacag aattcttcaa taaaatgaga       120
gatactctac cagctaaaga ctctaaatgg ttgaatccag catgtatgtt cggaggcaca       180
atgaatgata tagccgctct aggagagcca ttcagcgcaa agtgtcctcc tattgaagac       240
agtcttttat cgcacagata taaagactat gtggttaaat gggaaaggct agaaaagaat       300
agacggcgac aggtttctaa taaacgtgtt aaacatggtg atttatggat agccaactat       360
acatctaaat tcagtaaccg taggtatttg tgcaccgtaa ctacaaagaa tggtgactgt       420
gttcagggta tagttagatc tcatattaga aaacctcctt catgcattcc aaaaacatat       480
gaactaggta ctcatgataa gtatggcata gacttatact gtggaattct ttacgcaaaa       540
cattataata atataacttg gtataaagat aataaggaaa ttaatatcga cgatattaag       600
tattcacaaa cgggaaagaa attaattatt cataatccag agttagaaga tagcggaaga       660
tacgactgtt acgttcatta cgacgacgtt agaatcaaga atgatatcgt agtatcaaga       720
tgtaaaatac ttacggtttt accgtcacaa gaccacaggt ttaaactaaa aagaaattgc       780
ggatatgcgt caaattaa                                                    798
```